US008632976B2

(12) United States Patent
Bohannon et al.

(10) Patent No.: US 8,632,976 B2
(45) Date of Patent: Jan. 21, 2014

(54) **AMPLIFICATION OF TRP1 FOR SPECIFIC DETECTION OF *PHYTOPHTHORA RAMORUM***

(75) Inventors: Robert C. Bohannon, Elkhart, IN (US); Paul F. Russell, Jr., Elkhart, IN (US)

(73) Assignee: Agdia, Elkhart, IN (US)

( * ) Notice: Subject to any disclaimer, the term of this patent is extended or adjusted under 35 U.S.C. 154(b) by 58 days.

(21) Appl. No.: 13/008,192

(22) Filed: Jan. 18, 2011

(65) Prior Publication Data

US 2011/0177506 A1 Jul. 21, 2011

Related U.S. Application Data

(60) Provisional application No. 61/296,206, filed on Jan. 19, 2010.

(51) Int. Cl.
*C12Q 1/68* (2006.01)
*C12P 19/34* (2006.01)

(52) U.S. Cl.
USPC ........................... 435/6.12; 435/6.1; 435/6.11

(58) Field of Classification Search
None
See application file for complete search history.

(56) References Cited

PUBLICATIONS

Ioos et al., "Usefulness of single copy genes containing introns in Phytophthora for the development of detection tools for the regulated species *P. ramorum* and *P. fragariae,*" European Journal of Plant Pathology, 2006, vol. 116, pp. 171-176.*
Piepenburg et al., "DNA Detection Using Recombination Proteins," PLoS Biol., 2006, vol. 4, No. 7, e204, pp. 1115-1121.*
Goss, E.M. et al.; "Ancient isolation and independent evolution of the three clonal lineages of the exotic sudden oak death pathogen *Phytophthora ramorum.*"; 2009, *Molecular Ecology,* vol. 18, pp. 1161-1174.
Grünwald, N.J. et al.; "The Biology of *Phytophthora infestans* at Its Center of Origin"; 2005, *Ann. Rev. of Phytogathology,* vol. 43, pp. 171-190.
Hayden, K. et al.; "TaqMan Chemistry for *Phytophthora ramorum* Detection and Quantification, with a Comparison of Diagnostic Methods."; 2006, *Phytogathology,* vol. 96, No. 8, pp. 846-854.
Ivors, K. et al.; "AFLP and phylogenetic analyses of North American and European populations of *Phytophthora ramorum*" ; 2004, *Mycol. Res.,* vol. 108, pp. 378-392.
Ivors, K. et al.; "Microsatellite markers identify three lineages of *Phytophthora ramorum* in US nurseries, yet single lineages in US forest and European nursery populations "; 2006, *Molecular Ecology,* vol. 15, pp. 1493-1505.
Karlovsky P. et al.; "The TRP1 gene of *Phytophthora parasitica* encoding indole-3-glycerolphosphate synthase-N-(5'-phosphoribosyl) anthranilate isomerase: structure and evolutionary distance from homologous fungal genes"; 1991, *Gene,* vol. 109, pp. 161-165.
Prospero, S. et al.; "Population dynamics of the sudden oak death pathogen *Phytophthora ramorum* in Oregon from 2001 to 2004"; 2007, *Molecular Ecology,* vol. 16, pp. 2958-2973.
Rizzo, D.M. et al.; "*Phytophthora ramorum* as the Cause of Extensive Mortality of *Quercus* spp. and *Lithocarpus densiflorus* in California "; 2002, *Plant Disease,* vol. 86, pp. 205-214.
Rizzo, D.M. et al.; "*Phytophthora ramorum:* integrative research and management of an emerging pathogen in California and Oregon forests "; 2005, *Ann. Rev. of Phytogathology,* vol. 43, pp. 309-335.

* cited by examiner

*Primary Examiner* — Young J Kim
(74) *Attorney, Agent, or Firm* — Kilpatrick Townsend & Stockton LLP

(57) ABSTRACT

*Phytophthora ramorum* is currently a devastating disease for many plant species and infection presents significant economic problems, and in particular has lead to devastating effects on many specie of oak trees. The present invention provides methods and kits for selective detection of *Phytophthora ramorum* by amplification of indole-3-glycerol-phosphate synthase N-5'-phosphoribosyl anthranilate isomerase (trp1) in order to provide a method for detection of the presence of *P. ramorum* infection in a biological sample.

10 Claims, 15 Drawing Sheets

| P. ramorum, P. lateralis, & P. helicoides 11-09-09 | | | |
|---|---|---|---|
| Isolates Tested | Detected | Agdia # | Tube# |
| Phyt, species: ramorum | Yes | A35642 | 1 |
| Phyt, species: ramorum | Yes | A35642 | 2 |
| Phyt, species: lateralis | No | A37782 | 3 |
| Phyt, species: lateralis | No | A37782 | 4 |
| Pythium helicoides | No | A40766 | 5 |
| Pythium helicoides | No | A40766 | 6 |
| | | | |
| | | | |

| P. ramorum, P. cinnamomi, P. citrophthora, & P. dissotoum 11-09-09 | | | |
|---|---|---|---|
| Isolates Tested | Detected | Agdia # | Tube# |
| Phyt, species: ramorum: ID: P10090 | Yes | A35637 | 1 |
| Phyt, species: ramorum: ID: P11604 | Yes | A35643 | 2 |
| Phyt, species: ramorum: ID: P10102 | Yes | A35638 | 3 |
| Phyt, species: ramorum: ID: P1046 | Yes | A35636 | 4 |
| Phyt, species: ramorum: ID: P10641 | Yes | A35640 | 5 |
| Phyt, species: cinnamomi | No | A37786 | 6 |
| Phyt, species: citrophthora | No | A40764 | 7 |
| Pythium dissotoum, ID: Ph468 | No | A40765 | 8 |

| Tube #1 | 5'-1 vs 3'-1 |
|---|---|
| Tube #2 | 5'-2 vs 3'-1 |
| Tube #3 | 5'-3 vs 3'-1 |
| Tube #4 | 5'-4 vs 3'-1 |
| Tube #5 | 5'-5 vs 3'-1 |
| 5'-5 & 3'-1 is a possible alternate pairing | |

| Tube #1 | 5'-1 vs 3'-1 |
|---|---|
| Tube #2 | 5'-5 vs 3'-1 |
| Tube #3 | 5'-5 vs 3'-2 |
| Tube #4 | 5'-5 vs 3'-3 |
| Tube #5 | 5'-5 vs 3'-4 |
| Tube #6 | 5'-5 vs 3'-5 |
| Tube #7 | 5'-1 vs 3'-1 (b) |
| Tube #8 | 5'-5 vs 3'-1 (b) |

Figure 4: Large scale survey of Phytophthora and Pthium isolates. Runs 1-10b.

| Survey Run #1 12-04-09 | | | |
|---|---|---|---|
| Isolates Tested | Detected | Agdia # | Run#/Tube# |
| Phyt, species: Kelmania, ID: P11831 | No | 44470 | 1 / 1 |
| Phyt, species: cinnamomi, ID: P2040 | No | 44471 | 1 / 2 |
| Pythium species, ID: 8207. | No | 44472 | 1 / 3 |
| Phyt, species: kemoviae, ID: P10681. | No | 44473 | 1 / 4 |
| Phyt, species: ramorum, ID: P10085. | Yes | 44474 | 1 / 5 |
| Phyt, species: kelmania, ID: P10613. | No | 44475 | 1 / 6 |
| Phyt, species: cinnamomi, ID: P2040. | No | 44476 | 1 / 7 |
| Phyt, species: ramorum | Yes | A35642+ | 1 / 8 |

*FIGURE 4B*

Figure 4: Large scale survey of Phytophthora and Pythium isolates. Runs 1-10b.

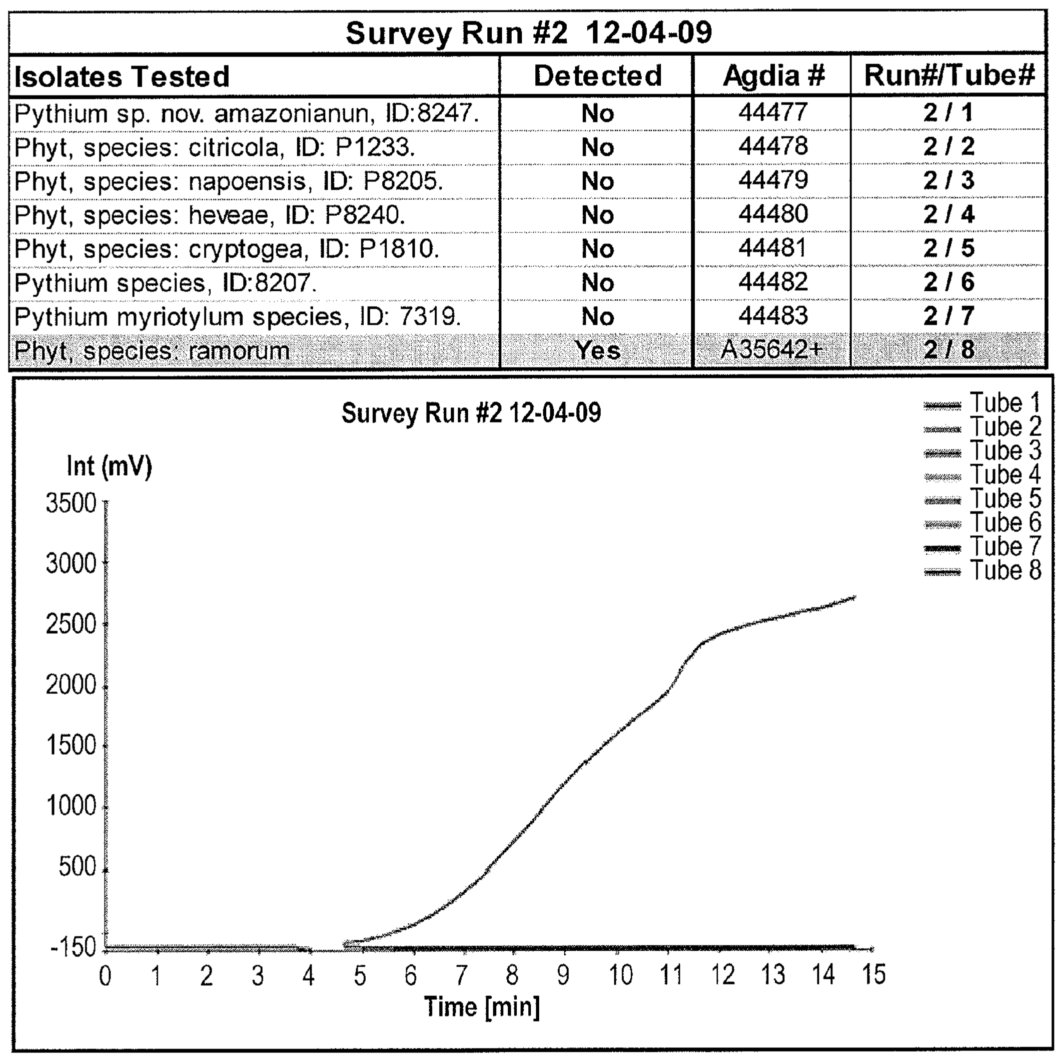

| Survey Run #2 12-04-09 | | | |
|---|---|---|---|
| **Isolates Tested** | **Detected** | **Agdia #** | **Run#/Tube#** |
| Pythium sp. nov. amazonianun, ID:8247. | **No** | 44477 | **2 / 1** |
| Phyt, species: citricola, ID: P1233. | **No** | 44478 | **2 / 2** |
| Phyt, species: napoensis, ID: P8205. | **No** | 44479 | **2 / 3** |
| Phyt, species: heveae, ID: P8240. | **No** | 44480 | **2 / 4** |
| Phyt, species: cryptogea, ID: P1810. | **No** | 44481 | **2 / 5** |
| Pythium species, ID:8207. | **No** | 44482 | **2 / 6** |
| Pythium myriotylum species, ID: 7319. | **No** | 44483 | **2 / 7** |
| Phyt, species: ramorum | **Yes** | A35642+ | **2 / 8** |

*FIGURE 4C*

Figure 4: Large scale survey of Phytophthora and Pythium isolates. Runs 1-10b.

| Survey Run #3 12-04-09 | | | |
|---|---|---|---|
| **Isolates Tested** | **Detected** | **Agdia #** | **Run#/Tube#** |
| Pythium species, ID: 8212. | **No** | 44484 | **3 / 1** |
| Phyt, species: crytogea, ID: P1088. | **No** | 44485 | **3 / 2** |
| Phyt, species: drechsleri, ID: P10331. | **No** | 44486 | **3 / 3** |
| Phyt, species: megasperma, ID: P1258. | **No** | 44487 | **3 / 4** |
| Phyt, species: cambivora, ID: P1735. | **No** | 44488 | **3 / 5** |
| Phyt, species: nicotianae, ID: P1926. | **No** | 44489 | **3 / 6** |
| Phyt, species: cactorum, ID: P6181. | **No** | 44490 | **3 / 7** |
| Phyt, species: ramorum | **Yes** | A35642+ | **3 / 8** |

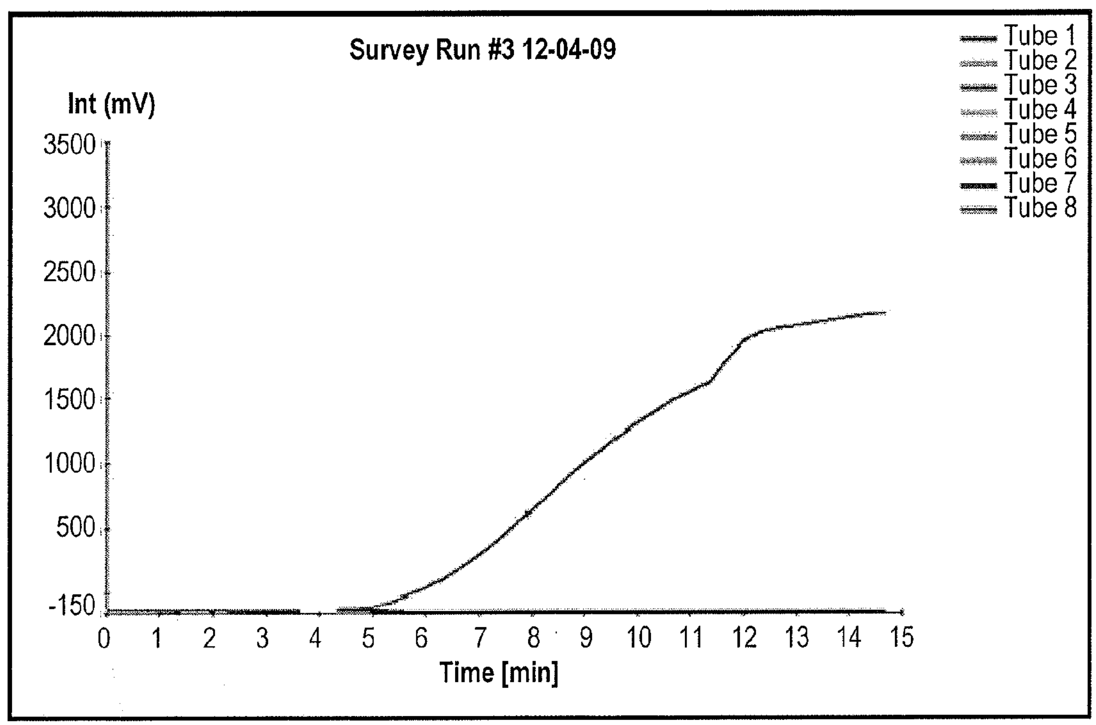

*FIGURE 4D*

Figure 4: Large scale survey of Phytophthora and Pythium isolates. Runs 1-10b.

| Survey Run #4 12-04-09 | | | |
|---|---|---|---|
| **Isolates Tested** | **Detected** | **Agdia #** | **Run#/Tube#** |
| Phyt, (#2), species: cactorum, ID: P6181. | **No** | 44491 | **4 / 1** |
| Phyt, species: boehmeriae, ID: P3970. | **No** | 44492 | **4 / 2** |
| Phyt, species: citrophthora, ID: P3525. | **No** | 44493 | **4 / 3** |
| Phyt, species: kernoviae, ID: P10681. | **No** | 44494 | **4 / 4** |
| Phyt, species: syringae, ID: P649. | **No** | 44495 | **4 / 5** |
| Phyt, species: syringae, ID: P7020. | **No** | 44496 | **4 / 6** |
| Phyt, species: syringae, ID: P3012. | **No** | 44497 | **4 / 7** |
| Phyt, species: ramorum | **Yes** | A35642+ | **4 / 8** |

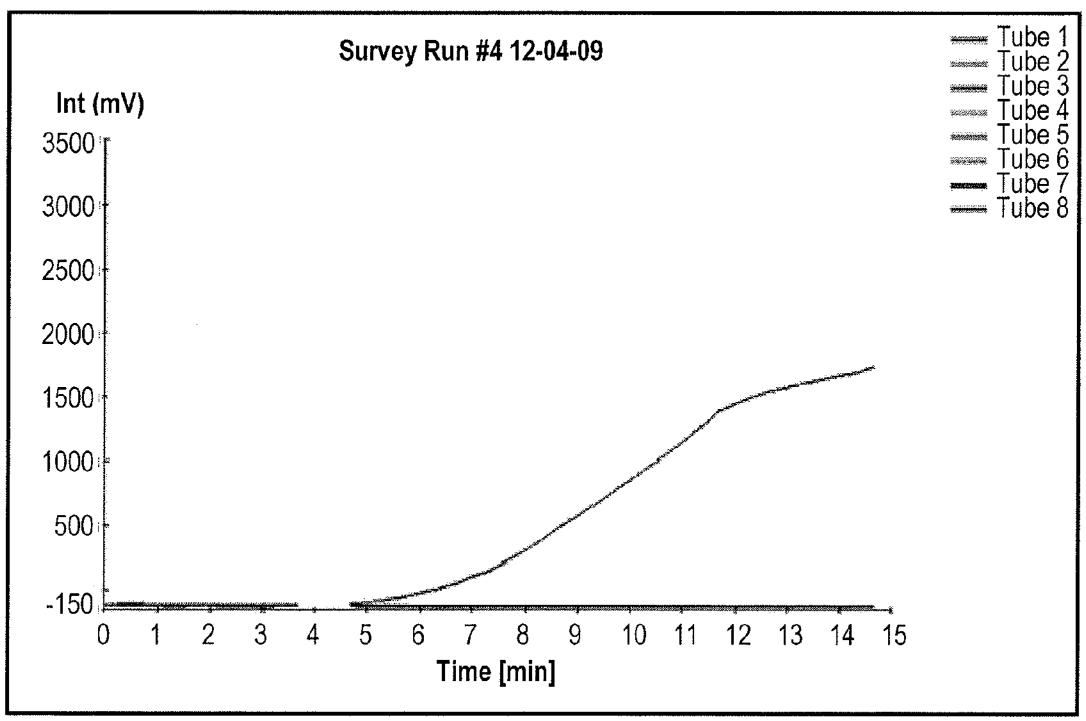

Figure 4: Large scale survey of Phytophthora and Pythium isolates. Runs 1-10b.

| Survey Run #5 12-04-09 | | | |
|---|---|---|---|
| Isolates Tested | Detected | Agdia # | Run#/Tube# |
| Phyt, (#2), species: syringae, ID: P649. | No | 44498 | 5 / 1 |
| Phyt, (#2), species: kernoviae, ID: P10681 | No | 44499 | 5 / 2 |
| Phyt, species: drechsleri, ID: P1740. | No | 44500 | 5 / 3 |
| Phyt, species: nicotianae, ID: P6262. | No | 44501 | 5 / 4 |
| Phyt, species: palmivora, ID: P3219. | No | 44502 | 5 / 5 |
| Pythium spp. ID: 19430. | No | 44503 | 5 / 6 |
| Pythium irregulare, ID: 15895. | No | 44504 | 5 / 7 |
| Phyt, species: ramorum | Yes | A35642+ | 5 / 8 |

*FIGURE 4F*

Figure 4: Large scale survey of Phytophthora and Pythium isolates. Runs 1-10b.

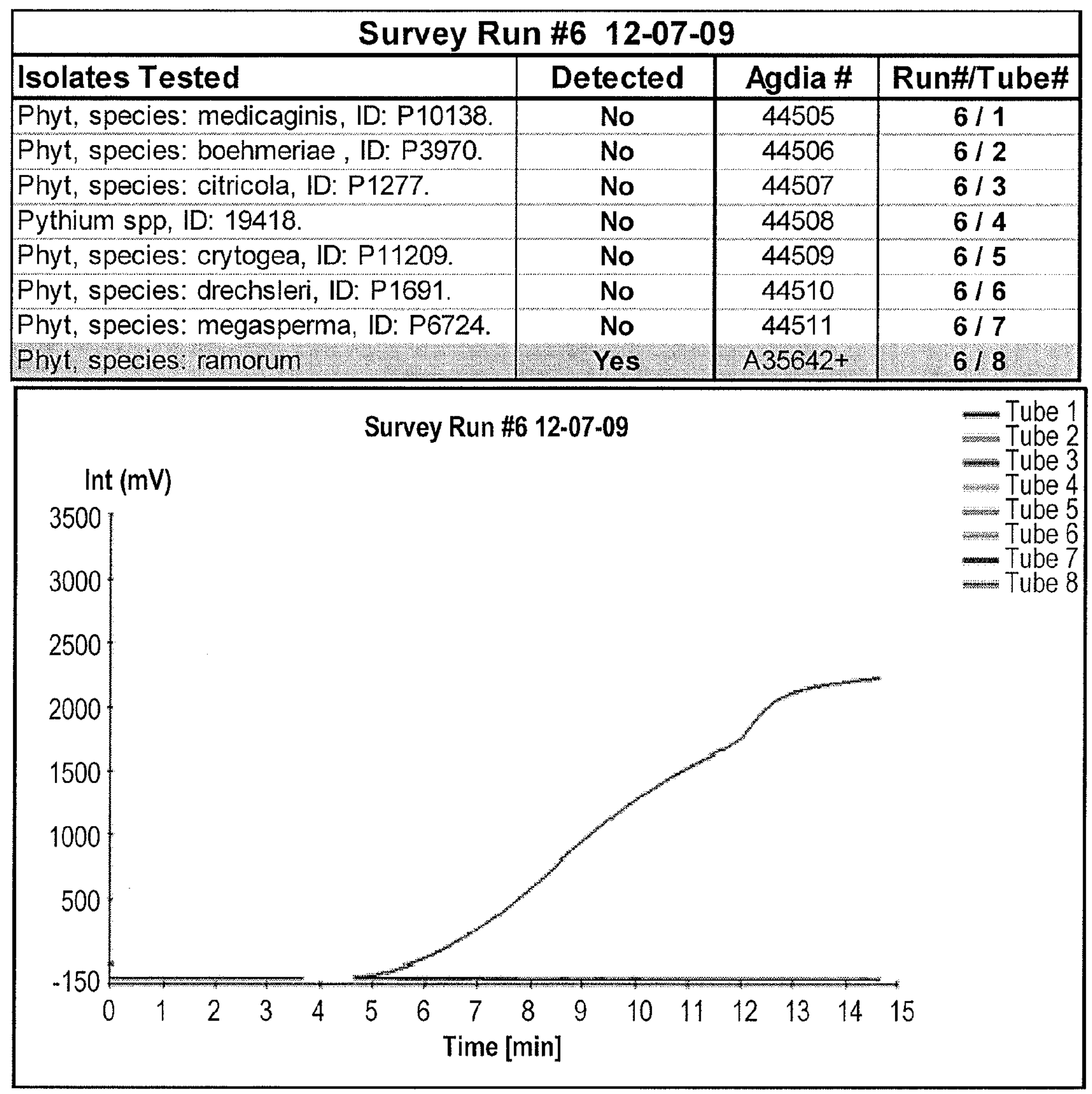

| Survey Run #6 12-07-09 | | | |
|---|---|---|---|
| **Isolates Tested** | **Detected** | **Agdia #** | **Run#/Tube#** |
| Phyt, species: medicaginis, ID: P10138. | No | 44505 | 6 / 1 |
| Phyt, species: boehmeriae , ID: P3970. | No | 44506 | 6 / 2 |
| Phyt, species: citricola, ID: P1277. | No | 44507 | 6 / 3 |
| Pythium spp, ID: 19418. | No | 44508 | 6 / 4 |
| Phyt, species: crytogea, ID: P11209. | No | 44509 | 6 / 5 |
| Phyt, species: drechsleri, ID: P1691. | No | 44510 | 6 / 6 |
| Phyt, species: megasperma, ID: P6724. | No | 44511 | 6 / 7 |
| Phyt, species: ramorum | Yes | A35642+ | 6 / 8 |

*FIGURE 4G*

Figure 4: Large scale survey of Phytophthora and Pythium isolates. Runs 1-10b.

| Survey Run #7 12-07-09 | | | |
|---|---|---|---|
| **Isolates Tested** | **Detected** | **Agdia #** | **Run#/Tube#** |
| Phyt, species: cryptogea f. sp. begoniae, | No | 44512 | 7 / 1 |
| Phyt, species: palmivora, ID: P10212. | No | 44513 | 7 / 2 |
| Phyt, species: megasperma, ID: P6727. | No | 44514 | 7 / 3 |
| Phyt, species: hungarica, ID: P9324. | No | 44515 | 7 / 4 |
| Phyt, species: tropicalis, ID: P16383. | No | 44516 | 7 / 5 |
| Pythium species, ID: 8204. | No | 44517 | 7 / 6 |
| Phyt, species: megasperma, ID: P10340. | No | 44518 | 7 / 7 |
| Phyt, species: ramorum | Yes | A35642+ | 7 / 8 |

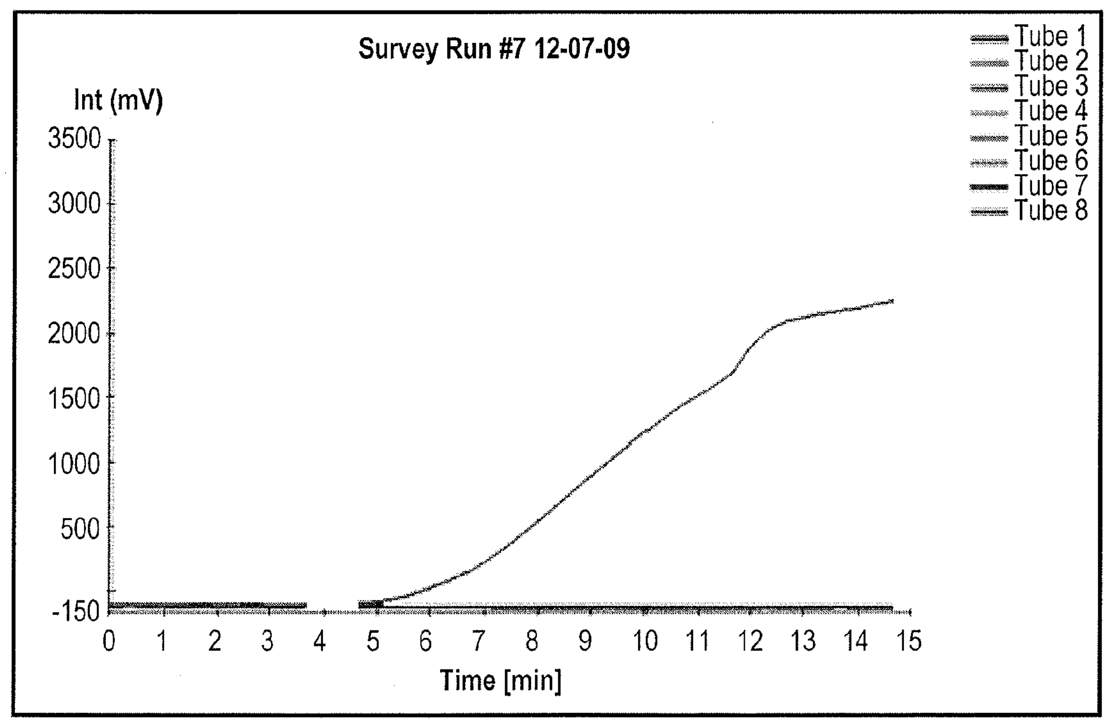

*FIGURE 4H*

Figure 4: Large scale survey of Phytophthora and Pythium isolates. Runs 1-10b.

| Survey Run #8 12-07-09 | | | |
|---|---|---|---|
| **Isolates Tested** | **Detected** | **Agdia #** | **Run#/Tube#** |
| Phyt, species: richardiae, ID: P7788. | No | 44519 | 8 / 1 |
| Phyt, species: cactorum, ID: P6221. | No | 44520 | 8 / 2 |
| Phyt, species: citricola, ID: P716. | No | 44521 | 8 / 3 |
| Phyt species, ID: P8219. | No | 44522 | 8 / 4 |
| Phyt, species: sinensis-type, ID: P1475. | No | 44523 | 8 / 5 |
| Phyt, species: megasperma, ID: P147. | No | 44524 | 8 / 6 |
| Phyt (#2), species: megasperma, ID: P14 | No | 44525 | 8 / 7 |
| Phyt, species: ramorum | Yes | A35642+ | 8 / 8 |

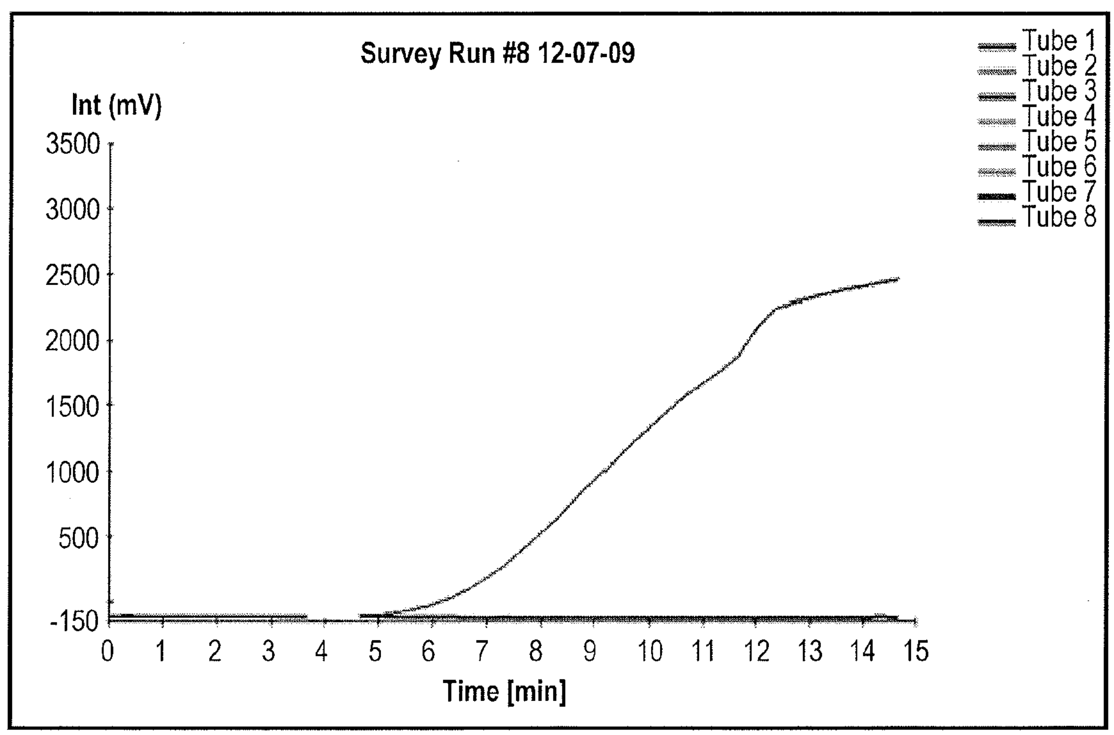

Figure 4: Large scale survey of Phytophthora and Pythium isolates. Runs 1-10b.

| Survey Run #9 12-07-09 | | | |
|---|---|---|---|
| Isolates Tested | Detected | Agdia # | Run#/Tube# |
| Phyt species, ID: P8219. | No | 44526 | 9 / 1 |
| Phyt, species: sojae, ID: P7428. | No | 44527 | 9 / 2 |
| Phyt, species: sinensis-type, ID: P1475. | No | 44528 | 9 / 3 |
| Phyt, species: palmivora, ID: P10212. | No | 44529 | 9 / 4 |
| Phyt, species: crytogea, ID: P11209. | No | 44530 | 9 / 5 |
| Phyt species, ID: P10665. | No | 44531 | 9 / 6 |
| Phyt, species: citricola-type, ID: P716. | No | 44532 | 9 / 7 |
| Phyt, species: ramorum | Yes | A35642+ | 9 / 8 |

*FIGURE 4J*

Figure 4: Large scale survey of Phytophthora and Pythium isolates. Runs 1-10b.

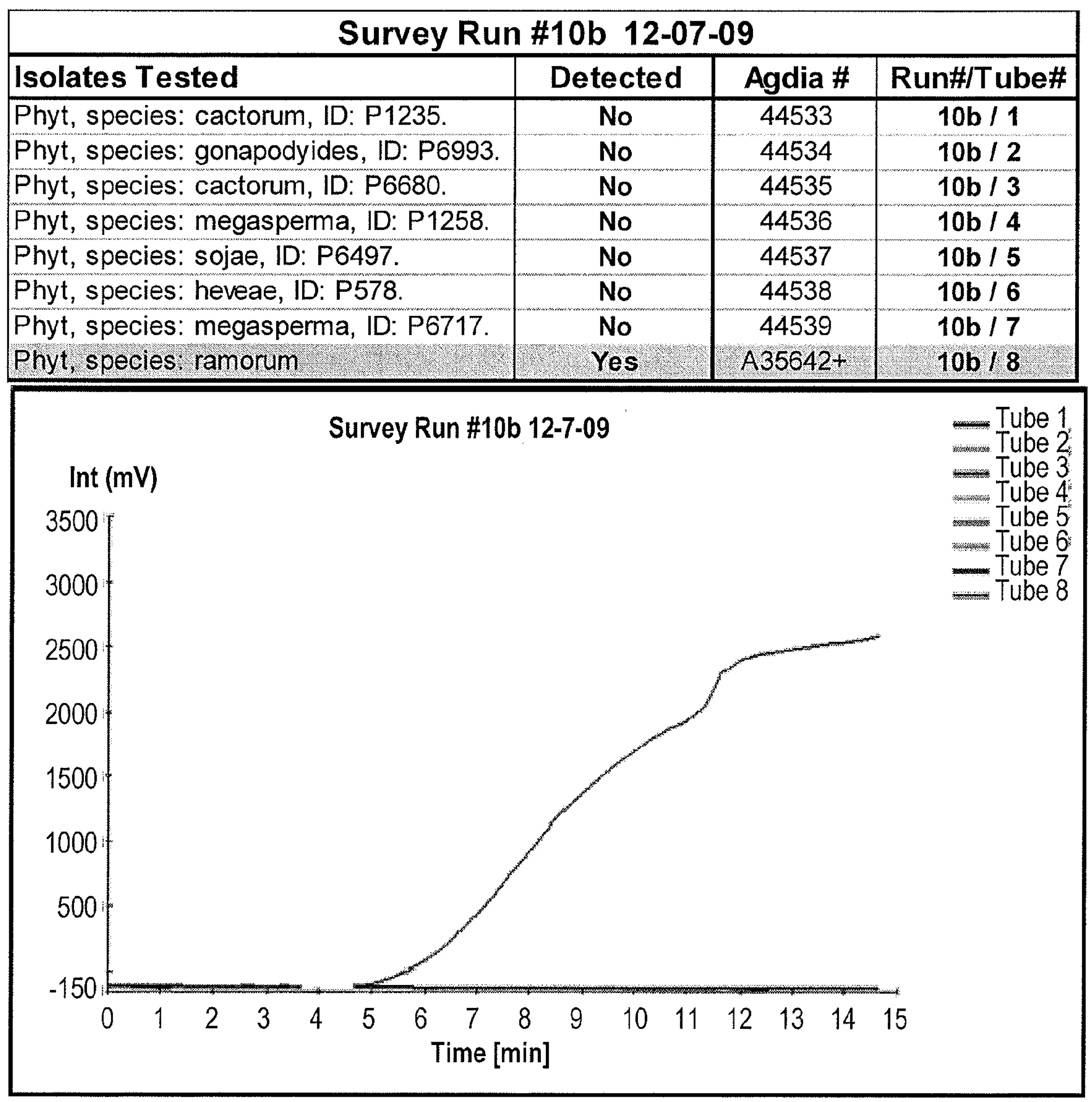

| Survey Run #10b 12-07-09 | | | |
|---|---|---|---|
| **Isolates Tested** | **Detected** | **Agdia #** | **Run#/Tube#** |
| Phyt, species: cactorum, ID: P1235. | **No** | 44533 | **10b / 1** |
| Phyt, species: gonapodyides, ID: P6993. | **No** | 44534 | **10b / 2** |
| Phyt, species: cactorum, ID: P6680. | **No** | 44535 | **10b / 3** |
| Phyt, species: megasperma, ID: P1258. | **No** | 44536 | **10b / 4** |
| Phyt, species: sojae, ID: P6497. | **No** | 44537 | **10b / 5** |
| Phyt, species: heveae, ID: P578. | **No** | 44538 | **10b / 6** |
| Phyt, species: megasperma, ID: P6717. | **No** | 44539 | **10b / 7** |
| Phyt, species: ramorum | **Yes** | A35642+ | **10b / 8** |

*FIGURE 5*

| Agdia # | Isolates Tested | Detected |
|---|---|---|
| 44522 | Phyt species, ID: P8219. | No |
| 44526 | Phyt species, ID: P8219. | No |
| 44531 | Phyt species, ID: P10665. | No |
| 44506 | Phyt, species: boehmeriae , ID: P3970. | No |
| 44492 | Phyt, species: boehmeriae, ID: P3970. | No |
| 44533 | Phyt, species: cactorum, ID: P1235. | No |
| 44490 | Phyt, species: cactorum, ID: P6181. | No |
| 44491 | Phyt, (#2), species: cactorum, ID: P6181. | No |
| 44520 | Phyt, species: cactorum, ID: P6221. | No |
| 44535 | Phyt, species: cactorum, ID: P6680. | No |
| 44488 | Phyt, species: cambivora, ID: P1735. | No |
| A37786 | Phyt, species: cinnamomi | No |
| 44471 | Phyt, species: cinnamomi, ID: P2040 | No |
| 44476 | Phyt, species: cinnamomi, ID: P2040. | No |
| 44478 | Phyt, species: citricola, ID: P1233. | No |
| 44507 | Phyt, species: citricola, ID: P1277. | No |
| 44521 | Phyt, species: citricola, ID: P716. | No |
| 44532 | Phyt, species: citricola-type, ID: P716. | No |
| A40764 | Phyt, species: citrophthora | No |
| 44493 | Phyt, species: citrophthora, ID: P3525. | No |
| 44512 | Phyt, species: cryptogea f. sp. begoniae, ID: P3265. | No |
| 44481 | Phyt, species: cryptogea, ID: P1810. | No |
| 44485 | Phyt, species: crytogea, ID: P1088. | No |
| 44509 | Phyt, species: crytogea, ID: P11209. | No |
| 44530 | Phyt, species: crytogea, ID: P11209. | No |
| 44486 | Phyt, species: drechsleri, ID: P10331. | No |
| 44510 | Phyt, species: drechsleri, ID: P1691. | No |
| 44500 | Phyt, species: drechsleri, ID: P1740. | No |
| 44534 | Phyt, species: gonapodyides, ID: P6993. | No |
| 44538 | Phyt, species: heveae, ID: P578. | No |
| 44480 | Phyt, species: heveae, ID: P8240. | No |
| 44515 | Phyt, species: hungarica, ID: P9324. | No |
| 44475 | Phyt, species: kelmania, ID: P10613. | No |
| 44470 | Phyt, species: Kelmania, ID: P11831 | No |
| 44473 | Phyt, species: kernoviae, ID: P10681. | No |
| 44494 | Phyt, species: kernoviae, ID: P10681. | No |
| 44499 | Phyt, (#2), species: kernoviae, ID: P10681 | No |
| A37782 | Phyt, species: lateralis | No |
| 44505 | Phyt, species: medicaginis, ID: P10138. | No |
| 44518 | Phyt, species: megasperma, ID: P10340. | No |
| 44487 | Phyt, species: megasperma, ID: P1258. | No |

*FIGURE 5 (cont'd)*

| | | |
|---|---|---|
| 44525 | Phyt (#2), species: megasperma, ID: P147 | No |
| 44536 | Phyt, species: megasperma, ID: P1258. | No |
| 44524 | Phyt, species: megasperma, ID: P147. | No |
| 44539 | Phyt, species: megasperma, ID: P6717. | No |
| 44511 | Phyt, species: megasperma, ID: P6724. | No |
| 44514 | Phyt, species: megasperma, ID: P6727. | No |
| 44479 | Phyt, species: napoensis, ID: P8205. | No |
| 44489 | Phyt, species: nicotianae, ID: P1926. | No |
| 44501 | Phyt, species: nicotianae, ID: P6262. | No |
| 44513 | Phyt, species: palmivora, ID: P10212. | No |
| 44529 | Phyt, species: palmivora, ID: P10212. | No |
| 44502 | Phyt, species: palmivora, ID: P3219. | No |
| A35636 | Phyt, species: ramorum: ID: P1046 | Yes |
| A35637 | Phyt, species: ramorum: ID: P10090 | Yes |
| A35638 | Phyt, species: ramorum: ID: P10102 | Yes |
| A35640 | Phyt, species: ramorum: ID: P10641 | Yes |
| A35642 | Phyt, species: ramorum | Yes |
| A35643 | Phyt, species: ramorum: ID: P11604 | Yes |
| 44474 | Phyt, species: ramorum, ID: P10085. | Yes |
| 44519 | Phyt, species: richardiae, ID: P7788. | No |
| 44523 | Phyt, species: sinensis-type, ID: P1475. | No |
| 44528 | Phyt, species: sinensis-type, ID: P1475. | No |
| 44537 | Phyt, species: sojae, ID: P6497. | No |
| 44527 | Phyt, species: sojae, ID: P7428. | No |
| 44495 | Phyt, species: syringae, ID: P649. | No |
| 44498 | Phyt, (#2), species: syringae, ID: P649. | No |
| 44497 | Phyt, species: syringae, ID: P3012. | No |
| 44496 | Phyt, species: syringae, ID: P7020. | No |
| 44516 | Phyt, species: tropicalis, ID: P16383. | No |
| A40765 | Pythium dissotoum, ID: Ph468 | No |
| A40766 | Pythium helicoides | No |
| 44504 | Pythium irregulare, ID: 15895. | No |
| 44483 | Pythium myriotylum species, ID: 7319. | No |
| 44477 | Pythium sp. nov. amazonianun, ID:8247. | No |
| 44517 | Pythium species, ID: 8204. | No |
| 44472 | Pythium species, ID: 8207. | No |
| 44484 | Pythium species, ID: 8212. | No |
| 44482 | Pythium species, ID:8207. | No |
| 44508 | Pythium spp, ID: 19418. | No |
| 44503 | Pythium spp. ID: 19430. | No |

AMPLIFICATION OF TRP1 FOR SPECIFIC DETECTION OF *PHYTOPHTHORA RAMORUM*

FIELD OF THE INVENTION

*Phytophthora ramorum* is currently a devastating pathogen for many plant species and infection is responsible for significant economic problems. The present invention provides methods and kits for selective detection of *Phytophthora ramorum* by amplification of indole-3-glycerol-phosphate synthase N-5'-phosphoribosyl anthranilate isomerase (trp1) in order to provide a method for detection of the presence of *P. ramorum* infection in biological samples.

BACKGROUND OF THE INVENTION

The *Phytophthora*, which literally means plant destroyer, is a genus of pathogens whose name was coined in 1861 by Anton de Barry when he showed that a species of *Phytophthora* was responsible for the Irish potato famine (Large, The advance of the fungi. Jonathan Cape, Ltd., London (1940)). The *Phytophthora* genus includes more than 65 plant pathogenic *oomycetes* species. These pathogens cause devastating diseases in numerous crops, ornamentals and native plants. The *Phytophthora* pathogens have an enormous impact on agriculture. (See, e.g., Govers and Gijzen, *Molecular Plant-Microbe Interactions,* 19:1295-1301 (2006)).

A recently emerged *Phytophthora* species, *Phytophthora ramorum*, is the causal agent for oak sudden death and is responsible for extensive mortality of coast live oak (*Quercus agrifolia*) and tan oak (*Lithocarpus densiflorus*) in northwest California (Rizzo et al., *Plant Disease,* 86:205-214. (2002); Rizzo et al., *Ann. Rev. of Phytopathology,* 43:309-335 (2005); Grünwald et al. *Ann. Rev. of Phytopathology,* 43:171-190 (2008)). *P. ramorum* additionally causes foliar lesions and twig dieback (Ramorum blight) on hosts in over 40 plant genera including many common ornamentals (Rizzo et al., *Ann. Rev. of Phytopathology,* 43:309-335 (2005). Further, the infestation of nursery stock has provided a mechanism for long-distance dispersal and quarantine efforts have led to large economic losses by the nursery industry in North American and Europe. (See, e.g., Goss et al., *Molecular Ecology,* 18:1161-1174 (2009).)

There are three clonal lineages of *P. ramorum*, within which genetic variation has only been observed at rapidly evolving microsatellites (Ivors et al., *Molecular Ecology,* 15:1493-1505 (2006)). Support for grouping isolates into three lineages comes from AFLP, microsatellites, and mitochondrial sequence data and is consistent across markers (Ivors et al., *Molecular Ecology,* 108:378-392 (2004); Ivors et al., *Molecular Ecology,* 15:1493-1505 (2006); Prospero et al., *Molecular Ecology,* 16:2958-2973 (2007); Martin, *Current Genetics,* 54:23-34(2008)). The EU1 lineage is responsible for all infestations in Europe but has also been found in nurseries on the West Coast of the USA. The NA1 genotype is the cause of the wildland epidemics in California and the southwest corner of Oregon and is also seen in nursery populations (Prospero et al., *Molecular Ecology,* 16:2958-2973 (2007)). The third genotype is the NA2 genotype and has only been observed in a limited number of nurseries. (See, e.g., Goss, et al., *Molecular Ecology,* 18:1161-1174 (2009).)

*P. ramorum* is self-sterile and sexual reproduction must occur between individual organisms of different mating types. The EU1 genotype is largely the A1 mating type and all tested NA1 and NA2 isolates have been A2 (Ivors et al., *Molecular Ecology,* 15:1493-1505 (2006)). The two mating types have been brought together by the nursery trade (Grünwald et al., *Plant Disease,* 92:314-314 (2008)), facilitating pathogen spread, and have both been detected in a California creek (Frankel, *Australasian Plant Pathology,* 37:19-25 (2008)). The closest known relatives of *P. ramorum* are *P. lateralis, P. foliorum*, and *P. hibernalis*, which together make up *Phytophthora* clade 8c (Blair et al., *Fungal Genetics and Biology,* 45:266-277 (2008)). (See, e.g., Goss, et al., *Molecular Ecology,* 18:1161-1174 (2009).)

Due to the devastating effects *P. ramorum* exhibits with respect to numerous plant species, selective detection of *P. ramorum* would prove highly useful and economically beneficial. The methods of the present invention provide for detection of indole-3-glycerol-phosphate synthase N-5'-phosphoribosyl anthranilate isomerase (trp1) in *Phytophthora ramorum* using isothermal amplification methods. The detection methods described allow for specific detection of the *P. ramorum* species of the *Phytophthora* genus even in the presence of closely related species.

In 1991, the TRP1 gene was isolated from *Phytophthora*, specifically *Phytophthora parasitica*, and shown to encode indole-3-glycerol-phosphate synthase N-5'-phosphoribosyl anthranilate isomerase (trp1, also known as IGPS-PRAI) (Karlovsky and Prell, *Gene,* 109:161-165 (1991)). The TRP1 gene encodes the bifunctional indole-3-glycerol-phosphate synthase N-5'-phosphoribosyl anthranilate isomerase enzyme (Karlovsky and Prell, *Gene,* 109:161-165 (1991). The bifunctional trp1 enzyme contains both indole-3-glycerol-phosphate synthase (IGPS) and phosphoribosyl anthranilate isomerase (PRAI) activities and is involved in tryptophan biosynthesis (Karlovsky and Prell, *Gene,* 109:161-165 (1991); Stryer, *Biochemistry,* 4$^{th}$ Edition, New York, 1975, 1981, 1988, 1995).

The trp1 gene is found in many *Phytophthora* species, as well as other bacterial and fungal species (Karlovsky and Prell, *Gene,* 109:161-165 (1991)). However, upon experimental examination of samples from many closely related *Phytophthora* species, the nucleic acid amplification methods of the present invention allow for detection of *P. ramorum* while not detecting any other *Phytophthora* species.

Any methods known to one of skill in art for amplification of polynucleotides can be employed with the methods of the present invention. However, traditional PCR methods require high temperatures to separate DNA strands and lower temperatures to allow primer binding, and as such require the reaction mixture and reaction chamber to cycle through hot and cold phases. Thus, traditional PCR methodologies require sophisticated and expensive equipment for precisely controlling the temperature during the amplification reaction period.

Alternatively, isothermal amplification methods exhibit many benefits over traditional PCR amplification methods. One such isothermal method is recombinase polymerase amplification (RPA), developed by Piepenburg, Armes and colleagues (Piepenburg et al., *PLOS Biology,* 4(7):1115-1121 (2006)). RPA employs recombinase-primer complexes that scan double-stranded DNA and facilitate exchange at cognate sites, allowing binding of opposing oligonucleotides primers to template DNA and subsequent extension by DNA polymerase (Piepenburg et al., *PLOS Biology,* 4(7):1115-1121 (2006)). This system allows for amplification of DNA without the need for precise temperature regulation or expensive and sophisticated equipment.

BRIEF SUMMARY OF THE INVENTION

In some embodiments the methods of the present invention provide for a method of specifically detecting the presence of

*Phytophthora ramorum* in a biological sample. In some embodiments the method comprises: (i) amplifying a region of the *P. ramorum* genome within the indole-3-glycerol-phosphate synthase N-5'-phosphoribosyl anthranilate isomerase (trp1) gene; and (ii) detecting the amplification product.

In some embodiments the method of specifically detecting the presence of *Phytophthora ramorum* in a biological sample comprises detection of a specific region. In some embodiments the specific region for amplification comprises nucleotides 86 to 325 of SEQ ID NO:1. In some embodiments specific region for amplification comprises nucleotides 108 to 325 of SEQ ID NO:1.

In some embodiments the method of specifically detecting the presence of *Phytophthora ramorum* in a biological sample requires amplification. In some embodiments the amplification is performed using an isothermal amplification system. In some embodiments the isothermal amplification system is a recombinase PCR system.

In some embodiments the specific region amplified by recombinase PCR using primers that bind to nucleotides is selected from the group consisting of nucleotides 86 to 394 of SEQ ID NO:1; nucleotides 94 to 327 of SEQ ID NO:1; nucleotides 96 to 325 of SEQ ID NO:1; nucleotides 110 to 314 of SEQ ID NO:1; nucleotides 86 to 325 of SEQ ID NO:1; and nucleotides 108 to 325 of SEQ ID NO:1.

In some embodiments the primers used for recombinase PCR amplification of the specific region are 5'-1 (SEQ ID NO:3) and 3'-1 (SEQ ID NO:8). In some embodiments the, primers used for recombinase PCR amplification of the specific region are 5'-5 (SEQ ID NO:7) and 3'-1 (SEQ ID NO:8).

In some embodiments the method of specifically detecting the presence of *Phytophthora ramorum* in a biological sample comprises detection using a fluorescent probe. In some embodiments the fluorescent probe binds to nucleotides 163 to 213 of SEQ ID NO:1. In some embodiments the fluorescent probe comprises SEQ ID NO:2.

In some embodiments the method of specifically detecting the presence of *Phytophthora ramorum* in a biological sample is performed in real time.

In some embodiments the biological samples for use in the methods of specifically detecting the presence of *Phytophthora ramorum* are from the genus *Quercus*.

In some embodiments the reagents for specific detection of *Phytophthora ramorum* in a biological sample are contained within a kit. In some embodiments the kit comprises: (i) an upstream and downstream amplification primer for amplifying a region of the *P. ramorum* genome within the indole-3-glycerol-phosphate synthase N-5'-phosphoribosyl anthranilate isomerase (trp1) gene; and (ii) non-specific amplification reagents for amplifying the trp1 gene.

In some embodiments the primers contained in the kit include primers capable of amplifying a region of the trp1 gene comprising nucleotides 86 to 325 of SEQ ID NO:1. In some embodiments the primers contain in the kit include primers capable of amplifying a region of the trp1 gene comprising nucleotides 108 to 325 of SEQ ID NO:1. In some embodiments the primers the primers contained in the kit are 5'-1 (SEQ ID NO:3) and 3'-1 (SEQ ID NO:8). In some embodiments the primers contained in the kit are 5'-5 (SEQ ID NO:7) and 3'-1 (SEQ ID NO:8).

In some embodiments the kit further comprises a nucleic acid probe that hybridizes to the amplified region of the trp1 gene. In some embodiments the kit further comprises a nucleic acid probe hybridizes to nucleotides 163 to 213 of SEQ ID NO:1. In some embodiments the kit further comprises a nucleic acid probe comprising SEQ ID NO:2. In some embodiments the kit comprises a nucleic acid probe that is fluorescently labeled.

In some embodiments the kit further comprises non-specific amplification reagents. In some embodiments the non-specific amplification reagents include a bacterial recombinase.

In some embodiments the kit further comprises a DNA intercalating agent to detect amplified DNA.

DEFINITIONS

The term "specifically detecting" or "specific detection" refers to identification or selection of a target nucleic acid sequence of *Phytophthora ramorum* within a population of *Phytophthora* and/or other closely related species in order to determine the presence of a *P. ramorum* microorganism that infects a member of the *Quercus* or *Lithocarpus* genera. Specific detection is limited to detection of a *P. ramorum* that infects a *Quercus* or *Lithocarpus* genera and does not include detection of other *Phytophthora* or other closely related organisms that infect a member of the *Quercus* or *Lithocarpus* genera. The target nucleic acid can be in the context of genomic DNA, RNA, amplification products or other extraneous material.

The term "*Phytophthora ramorum*" refers to a specific species of a genus of plant-damaging *oomycetes*, whose member species infect and kill oaks and other species of trees and plants. Symptoms of *P. ramorum* include bleeding cankers on the tree's trunk and dieback of the foliage, in many cases eventually leading to the death of the tree. *P. ramorum* also infects a great number of other plant species, significantly rhododendrons, causing a non-fatal foliage disease known as *ramorum* dieback. Infected plants can act as sources of the inoculums for the disease, and the pathogen producing spores can be transmitted by wind and rainwater.

The term "trp1" refers to the indole-3-glycerol-phosphate synthase N-5'-phosphoribosyl anthranilate isomerase (trp1, also known as IGPS-PRAI), and includes polynucleotide sequences having both indole-3-glycerol-phosphate synthase (IGPS) and phosphoribosyl anthranilate isomerase (PRAI) activities, having substantial identity to SEQ ID NO:1 and that further comprise a portion of nucleotides 86 to 394 of SEQ ID NO:1 which allows for specific detection of a *P. ramorum* that infects a member of the *Quercus* or *Lithocarpus* genera. The term "substantial identity" in the context of polynucleotide sequences means that a polynucleotide comprises a sequence that has at least 50% sequence identity to all of SEQ ID NO:1 and further comprises a portion of nucleotides 86 to 394 of SEQ ID NO:1 which allows for specific detection of a *P. ramorum* that infects a member of the *Quercus* or *Lithocarpus* genera. Percent identity can be any integer from 50% to 100%. Exemplary embodiments include at least: 50%, 55%, 60%, 65%, 70%, 75%, 80%, 85%, 90%, 95%, or 99% compared to a reference sequence using programs described herein or others well know to one of skill in the art; preferably BLAST using standard parameters, as described below. Accordingly, the trp1 sequences of the invention can include nucleic acid sequences that have substantial identity to SEQ ID NO:1 and comprise a portion of nucleotides 86 to 394 of SEQ ID NO:1 which allows for specific detection of a *P. ramorum* that infects a member of the *Quercus* or *Lithocarpus* genera; a nucleotide sequence that comprises a portion of SEQ ID NO:1 and further comprises a portion of nucleotides 86 to 394 of SEQ ID NO:1 which allows for specific detection of a *P. ramorum* that infects a member of the *Quercus* or *Lithocarpus* genera; or a sequence comprising SEQ ID NO:1.

Standard BLAST algorithm parameters have an expected threshold of 10 (according to the stochastic model of Karlin and Altschul (*PNAS,* 87:2264-2268(1990)); a word size of 28; reward and penalty of 1/−2 (a ratio of 0.5, or 1/−2, is used for sequences that are 95% conserved); and a linear GAP cost.

Optimal alignment of sequences for comparison can also be conducted by the local homology algorithm of Smith and Waterman Add. *APL. Math.* 2:482 (1981), by the homology alignment algorithm of Needle man and Wunsch *J. Mol. Biol.* 48:443 (1970), by the search for similarity method of Pearson and Lipman *Proc. Natl. Acad. Sci*. (U.S.A.) 85: 2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), Karlin and Altschul *Proc. Natl. Acad. Sci*. (U.S.A.) 87:2264-2268(1990), or by inspection.

The term "detect" or "detecting" or variants thereof include both quantitative and qualitative methods of detection. Any methods well known to one of skill in the art for detection of nucleic acids can be employed in the methods of the present invention and includes those listed as well as other well known to those skilled in the art.

The term "amplified product" or "amplification product" or variants thereof can include any polynucleotide generated as a copy of an original sequence and/or a complementary sequence of target nucleotide sequence. The target nucleic acid variant amplified can be RNA or DNA or a modification thereof. If the target nucleic acid is RNA, the RNA can be directly amplified or can first be reversed transcribed into cDNA using a reverse transcriptase primer and reverse transcriptase by methods well known to those of skill in the art.

The term "recombinase amplification" refers to a method of isothermal amplification where a recombinase-primer complex is employed to facilitate strand separation and primer binding. One example of recombinase amplification is recombinase polymerase amplification (RPA), developed by Piepenburg, Armes and colleagues (Piepenburg et al., *PLOS Biology,* 4(7):1115-1121 (2006)), incorporated herein by reference in its entirety. RPA employs recombinase-primer complexes that scan double-stranded DNA and facilitate exchange at cognate sites, allowing binding of opposing oligonucleotides primers to template DNA and subsequent extension by DNA polymerase (Piepenburg et al., *PLOS Biology,* 4(7):1115-1121 (2006)).

The term "isothermal amplification system" refers to an amplification system or an amplification reaction wherein the amplification reaction occurs without a requirement for changes in temperature. Examples of isothermal amplification include recombinase polymerase amplification, ramification amplification methods, helicase-dependent amplification as described herein, as well as others well known to one skilled in the art.

The terms "primer" or "primers" refer to any oligonucleotide sequence that can hybridize or bind to a target nucleic acid sequence. Examples of primers utilized by the methods of the present invention include 5'-1 (SEQ ID NO:3), 5'-2 (SEQ ID NO:4), 5'-3 (SEQ ID NO:5), 5'-4 (SEQ ID NO:6), 5'-5 (SEQ ID NO:7), 3'-1 (SEQ ID NO:8), 3'-2 (SEQ ID NO:9), 3'-3 (SEQ ID NO:10), 3'-4 (SEQ ID NO:11) and 3'-5 (SEQ ID NO:12).

The term "fluorescent probe" refers to any oligonucleotide sequence containing a label that under appropriate conditions is capable of emitting photons of light (a fluorophore) and that is capable of binding or hybridizing to a target nucleic acid sequence. Any fluorescent label or fluorophore known to one of skill in the art can be employed in the methods of the present invention. Examples of fluorescent labels include but are not limited to Fluorescein, TAMRA, rhodamines (including TMR, ROX, Texas red, Rhodamine 6G, Rhodamine Green, Rhodamine Red), Alexa fluors, Dylight Fluors, ATTO Dyes, FAM, TET, HEX, Cy2, Cy3, Cy3.5Cy5, Cy5.5, Cy7LC red 640, and LC red 706, Acridine, AMCA, Edans, Eosin, Erythrosin, Joe, LightCycler, NBD, Rhodol Green, ROX, NED, and VIC. The oligonucleotide containing the fluorescent label can further contain a quenching moiety. Examples of quenching moieties include Black Hole Quenchers (BHQ1 and BHQ2), dabcyl and Iowa Black™ FQ/RQ. In some embodiments the quencher is located between 1 and 6 bases from the fluorophore. An example of a fluorescent probe that can be used with the methods of the present invention includes Probe-r (SEQ ID NO:2). (See, e.g., Marras, "Selection of Fluorophore and Quencher Pairs for fluorescent Nucleic Acid hybridization Probes" from *Methods in Molecular Biology: Fluorescent Energy Transfer Nucleic Acid Probes: Designs and Protocols*. Edited by: V. V. Didenko (2006); Ausubel, et al. Editor, *Current Protocols in Molecular Biology*, USA, 1984-2008; and Behlke et al., Fluorescence and Fluorescence Applications, Integrated DNA Technologies located on the World Wide Web at idtdna.com/support/technical/TechnicalBulletinPDF/Fluorescence_and_Fluorescence_Applications.pdf.)

The term "real-time" detection in the context of amplification indicates an amplification reaction for which the amount of reaction product, i.e. the amplicon or amplification product, is monitored simultaneously with the reaction progression. During real-time detection, amplification products are monitored and quantitated as the amplification products are generated in the reaction mixture.

The term "biological sample" or variants thereof can include any sample obtained from a plant species. In some embodiments, a biological sample can include but is not limited to leaves, stems, flowers, portions of the trunk of a tree or any other portion of a plant that is readily accessible for sampling and from which DNA can be obtained.

The term "oak tree" includes any species of oak that is, can be or could be infected or affected by the *P. ramorum* pathogen. Examples of oak trees include but are not limited to tan oaks, coast live oaks, black oaks and Shreve's oaks, as well as other members of the *Quercus* or *Lithocarpus* genera.

The term "non-specific amplification reagents" includes any agents in the reaction mixture which are required for or involved with amplification of the target nucleic acid but which are not primers or probes, i.e., those agents that do not hybridize with other nucleic acids in the reaction mixture. Examples of non-specific amplification reagents can include but are not limited to buffers, salts, metals, ions, unincorporated nucleotides, excess labels, additional necessary proteins (including the single-stranded binding protein RPA) and enzymes (including bacterial recombinase).

The term "bacterial recombinase" refers to a bacterial enzyme that is capable of forming an enzyme complex with a primer, facilitating nucleic acid strand exchange, and subsequently allowing for primer binding to the template nucleic acid upon which strand exchange has occurred.

The term "hybridizes" or "hybridize" or "hybridization" or variants thereof indicates the process during which, under suitable conditions, two nucleic sequences bond to one another with stable and specific hydrogen bonds so as to form a double strand. These hydrogen bonds form between the complementary bases adenine (A) and thymine (T) (or uracil (U)) or between the complementary bases guanine (G) and cytosine (C). In some embodiments, the hybridization of two nucleic sequences can be total (indicating complementary sequences), i.e., the double strand obtained during this hybridization comprises only A-T bonds and C-G bonds. In some embodiments, the hybridization may be partial (indicating sufficiently complementary sequences), i.e., the double strand obtained comprises sufficient A-T bonds and C-G bonds to allow the double strand to form, but also contains bases not bonded to a complementary base. The hybridization between two complementary sequences or sufficiently complementary sequences depends on the operating conditions that are used and the number of mismatches. Nucleic acid hybridization methods are described in Sambrook et al. Molecular Cloning: A Laboratory Manual, 2$^{nd}$ Edition, New York, 1989; Haymes et al., *Nucleic Acid Hybridization: A Practical Approach*, Washington, D.C., 1985; and Ausubel, et al. Editor, Current Protocols in Molecular Biology, USA, 1984-2008, incorporated herein by reference in their entirety.

The term "intercalating agent" refers to a molecule that binds to a nucleic acid independent of the sequence of the nucleic acid. Examples of intercalating agents include but are not limited to SYBR green, SYBR gold, ethidium bromide (EtBr), ICR-191, amsacrine and doxorubicin (Dox), as well as others well known to one of skill in the art. Intercalating agents can be used in conjunction with the methods of detection of the present invention and any intercalating agent well known to one of skill in the art can be employed.

The terms "comprise" or "comprising" or "include" or "including" or variants thereof are used in the "open" sense such that the terms are inclusive and permit the presence of additional elements. The terms specify the presence of the stated features, steps, or components as recited without precluding the presence or addition of one or more features, steps, or components.

BRIEF DESCRIPTION OF THE DRAWINGS

FIG. 1 illustrates the use of the TwistAmp™ Exo Kit for specific identification of *P. ramorum*. The oligonucleotide set consisting of primers 5'-1 (SEQ ID NO:3) and 3'-1 (SEQ ID NO:8) and the TAMRA labeled Probe-r (SEQ ID NO:2) is capable of specific identification of trp1 from *P. ramorum* in the presence of the closely related *P. lateralis* and *P. helicoides*.

FIG. 2 illustrates the use of the TwistAmp™ Exo Kit for specific identification of *P. ramorum*. The oligonucleotide set consisting of primers 5'-1 (SEQ ID NO:3) and 3'-1 (SEQ ID NO:8) and the TAMRA labeled Probe-r (SEQ ID NO:2) is capable of specific identification of trp1 from *P. ramorum* in the presence of the closely related *P. cinnamomi* and *P. citrophthora*, as well as in the presence of *Pythium dissotoum.*

FIG. 3 illustrates the use of the TwistAmp™ Exo Kit for optimization of primer pairs for detection of *P. ramorum*. Different combinations of primers were screened in order to optimize primer pairing. Initially, all upstream 5' primers (SEQ ID NOS:3-7) were paired with the primer 3'-1 (SEQ ID NO:8). As seen in FIG. 3A, the optimal pairing was with primers 5'-1 (SEQ ID NO:3) and 3'-1 (SEQ ID NO:8). Next, the best 5' primer (5'-1 (SEQ ID NO:3)) was paired with all downstream 3' primers (SEQ ID NOS:8-12). All combinations were tested against *P. ramorum* strain A35642 and were compared to the original primer pair 5'-1 (SEQ ID NO:3)/3'-1 (SEQ ID NO:8). As seen FIG. 3B, primer 5'-5 (SEQ ID NO:12) also worked optimally with 3'-1, exhibiting detection signals similar to the 5'-1 (SEQ ID NO:3)/3'-1 (SEQ ID NO:8) primer pair. For these experiments, no primer from the 3' region performed as well as the 3'-1 (SEQ ID NO:8) primer. Final analysis of reactivity showed the original pair, 5'-1 (SEQ ID NO:3)/3'-1 (SEQ ID NO:8), produced faster amplification, potentially translating to a more rapid and sensitive test.

FIG. 4 illustrates the use of the TwistAmp™ Exo Kit for specific identification of *P. ramorum*. The oligonucleotide set consisting of primers 5'-1 (SEQ ID NO:3) and 3'-1 (SEQ ID NO:8) and the TAMRA labeled Probe-r (SEQ ID NO:2) is capable of specific identification of trp1 from *P. ramorum* in the presence of the closely related *P. kelmania, P. cinnamomi* and *P. kernoviae*, as well as in the presence of *Pythium* species (FIG. 4A). The oligonucleotide set consisting of primers 5'-1 (SEQ ID NO:3) and 3'-1 (SEQ ID NO:8) and the TAMRA labeled Probe-r (SEQ ID NO:2) is capable of specific identification of trp1 from *P. ramorum* in the presence of the closely related *P. citricola, P. napoensis, P. heveae, P. cryptogea*, as well as in the presence of *Pythium amazonianun* and *Pythium myriotylum* (FIG. 4B). The oligonucleotide set consisting of primers 5'-1 (SEQ ID NO:3) and 3'-1 (SEQ ID NO:8) and the TAMRA labeled Probe-r (SEQ ID NO:2) is capable of specific identification of trp1 from *P. ramorum* in the presence of the closely related *P. cryptogea, P. drechsleri, P. megasperma, P. cambivora, P. nicotianae*, and *P. cactorum* (FIG. 4C). The oligonucleotide set consisting of primers 5'-1 (SEQ ID NO:3) and 3'-1 (SEQ ID NO:8) and the TAMRA labeled Probe-r (SEQ ID NO:2) is capable of specific identification of trp1 from *P. ramorum* in the presence of the closely related *P. cactorum, P. boehmeriae, P. citrophthora, P. kernoviae*, and *P. syringae* (FIG. 4D). The oligonucleotide set consisting of primers 5'-1 (SEQ ID NO:3) and 3'-1 (SEQ ID NO:8) and the TAMRA labeled Probe-r (SEQ ID NO:2) is capable of specific identification of trp1 from *P. ramorum* in the presence of the closely related *P. syringae, P. kernoviae, P. drechsleri, P. nicotianae, P. palmivora*, as well as in the presence of *Pythium* spp. and *Pythium irregulare* (FIG. 4E). The oligonucleotide set consisting of primers 5'-1 (SEQ ID NO:3) and 3'-1 (SEQ ID NO:8) and the TAMRA labeled Probe-r (SEQ ID NO:2) is capable of specific identification of trp1 from *P. ramorum* in the presence of the closely related *P. medicaginis, P. boehmeriae, P. citricola, P. cryptogea, P. drechsleri* and *P. megasperma*, as well as in the presence of *Pythium* spp.

FIG. 5: Summary of Large Scale Survey of TwistAmp™ Specific Detection of *P. ramorum*. FIG. 5 provides a table containing a summary of the results from the use of the TwistAmp™ Exo Kit for specific identification of *P. ramorum*. Summary of results of specific detection of *P. ramorum* in samples run in the presence of closely related *Phytophthora* species, as well as in the presence of several *Pythium* species. In all samples tested, *P. ramorum* was specifically detected while other *Phytophthora* and *Pythium* species were not detected.

DETAILED DESCRIPTION

I. Sample Preparation

Figure 1:
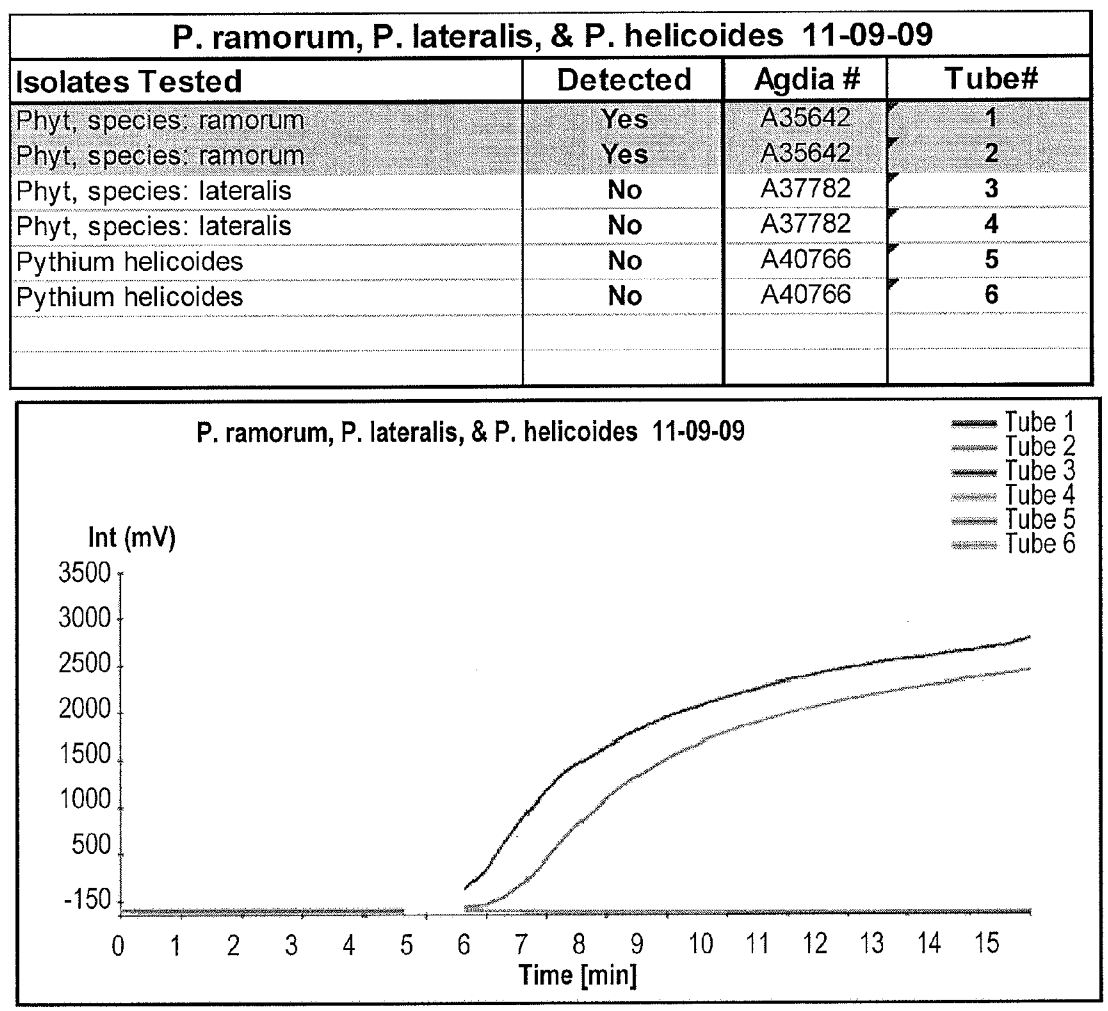
FIG. 1: Specific Detection of *P. ramorum* using TwistAmp™.

Samples can be prepared by any methods well known to one skilled in the art. For example, Danks et al., WO 2007/104962, incorporated herein by reference in its entirety, describes preparation of rhododendron samples that are obtained by harvesting a leaf and cutting into small piece using a scalpel blade, placing into an LFD extraction bottle, from an LFD kit obtained from Pocket Diagnostics™ (CSL, York, UK), and processing according to the manufacturer's instructions. Other commercially available kits for sample preparation include the Plant/Fungal Isolation Kit (Product #26200) and the Fungi/Yeast Genomic DNA Isolation Kit (Product #27300), both available from Norgen Biotek Corporation (Ontario, Canada); RNeasy Plant Mini or Maxi Kits available from Qiagen (USA); DNeasy Plant Mini or Maxi Kits available from Qiagen (USA); or Ultraclean Plant RNA or Ultraclean Plant DNA isolation kits available from MoBio Laboratories (California, USA). Further, any other methods well known to one of skill in the art for preparation of samples can be employed with the methods of the present invention.

Samples can be obtained from any plant species for examination of infection with *P. ramorum*. Samples can be obtained from plants including for example but not limited to oak trees (including tan oaks, coast live oaks, black oaks and Shreve's oaks) and rhododendrons, as well as the list of plants included in Table 1 below. (See, e.g., Information located on the World Wide Web at aphis.usda.gov/plant_health/and aphis.usda.gov/plant_health/plant_pest_info/pram/index.shtml.)

TABLE 1

Animal and Plant Health Inspection Service (APHIS) List of Regulated Hosts and Plants Associated with *Phytophthora ramorum*

| Scientific Name (45) | Common Name(s) |
|---|---|
| *Acer macrophyllum* | Bigleaf maple |
| *Acer pseudoplatanus** | Planetree maple |
| *Adiantum aleuticum* | Western maidenhair fern |
| *Adiantum jordanii* | California maidenhair fern |
| *Aesculus californica* | California buckeye |
| *Aesculus hippocastanum** | Horse chestnut |
| *Arbutus menziesii* | Madrone |
| *Arctostaphylos manzanita* | Manzanita |
| *Calluna vulgaris* | Scotch heather |
| *Camellia* spp. | *Camellia* - all species, hybrids and cultivars |
| *Castanea sativa* | Sweet chestnut |
| *Fagus sylvatica** | European beech |
| *Frangula californica* (≡*Rhamnus californica*) | California coffeeberry |
| *Frangula purshiana* (≡*Rhamnus purshiana*) | Cascara |
| *Fraxinus excelsior* | European ash |
| *Griselinia littoralis* | *Griselinia* |
| *Hamamelis virginiana* | Witch hazel |
| *Heteromeles arbutifolia* | Toyon |
| *Kalmia* spp. | Mountain laurel - all species, hybrids and cultivars |
| *Lithocarpus densiflorus** | Tanoak |
| *Lonicera hispidula* | California honeysuckle |
| *Laurus nobilis* | Bay laurel |
| *Magnolia doltsopa* = *Michelia doltsopa* | *Michelia* |
| *Maianthemum racemosum* (≡*Smilacina racemosa*) | False Solomon's seal |
| *Parrotia persica* | Persian ironwood |
| *Photinia fraseri* | Red tip *photinia* |

A sample for the methods of the present invention can include but is not limited to plant tissue (including leaves, seeds, petals, flowers, bark, etc.), plant body fluid, an extract from a cell, chromosome, organelle; genomic DNA, RNA or cDNA in solution or bound to a substrate; a cell; a tissue; a tissue print; and the like. In this context "substrate" refers to any rigid or semi-rigid support to which nucleic acid molecules or proteins are bound and includes membranes, filters, chips, slides, wafers, fibers, magnetic or nonmagnetic beads, gels, capillaries or other tubing, plates, polymers, and microparticles with a variety of surface forms including wells, trenches, pins, channels and pores. A substrate may also refer to a reactant in a chemical or biological reaction, or a substance acted upon (e.g., by an enzyme).

II. Amplification of trp1

As stated previously, indole-3-glycerol-phosphate synthase N-5'-phosphoribosyl anthranilate isomerase (trp1) is involved in tryptophan biosynthesis. A partial trp1 sequence is publically available and is listed under GenBank Accession Number EU851002 (SEQ ID NO:1) as:

```
AGCAGGTCGTGACGCCCGAGCAGCTGGTGAAGAAGATCGAGAGCACCGA

GAGTGTCTACGGCTCGGCCCTGCGCGTGCTCGACCGCCTCAACGCGCCG

GTGGTGCGTCCCCAGAGTAGAAACTTCGGGAATGGACGAGGCTGACGGC

TGTCGTTGCATTGTTCCTATTGTTGTATTGCAATATCACAGAAGGAAGG

CTGGTCGGACGTGGCGCTGGCAGCCGAGTTCAAGCGCGCCAGCCCCAGC

AAGGGAGATATCGCCACGGGACTCAACCTGCGCGGTGCGTGGCGGCTGT

ATTGCTGCAAGTATAGGAGGAGGAAGACGGGAGCTAATGTGATTTTTGC

AATGGGAGCAGAGCAAGTCAAGTCGTATGCGGACGCGGGCGCCAGCATG

ATCTCCGTGCTGACGGAGCCCAAGTGGTTCAAGGGCTCATTGGAGGACA

TGATGGCGGCCAGAGACGTGGTGGAGAGCATGAGCGCTCGCCCCGCCAT

CCTCCGCAAGGACTTCATTATCGACGTGTACCAGCTGCTGGAGGCTCGC

GCCTACGGAGCCGACTGTGTGCTGCTCATTGTGGCGCTGCTGTCCCAGG

AGCAGCTCGTTGAGCTCATTGATGCAAGTAGCTGCGTTAATGAGCCGAA
```

-continued

```
CTTTCTGACGAGAGGATGAATGTTGACGTTGAGTTTGTGTCTGCTTTGC

ATTGTGCAGGCAACTCACAACCTCGGCATGTGCGCCTTAGTGGAGGTGA

ACAGCGTTGAGGAGCTGGACATCGCGCTGGCTGCCAGGTCGCGCCTGAT

TGGCGTCAATAACCGAGACCTCC
```

Despite being present in multiple species of *Phytophthora*, the trp1 gene contains a region that allows for specific detection of *P. ramorum* within a population of *Phytophthora* and/or other closely related species, wherein the *P. ramorum* infects a member of the *Quercus* or *Lithocarpus* genera. For the methods of detection of *P. ramorum* described in the present invention, the following primers were employed for amplification of *P. ramorum* trp1.

| Twisted primers: |
|---|
| 5'-1 (33mer) (SEQ ID NO: 3)<br>5'-CCCCAGAGTAGAAACTTCGGGAATGGACGAGGC |
| 5'-2 (33mer) (SEQ ID NO: 4)<br>5'-CCAGAGTAGAAACTTCGGGAATGGACGAGGCTG |
| 5'-3 (33mer) (SEQ ID NO: 5)<br>5'-CCGGTGGTGCGTCCCCAGAGTAGAAACTTCGGG |
| 5'-4 (33mer) (SEQ ID NO: 6)<br>5'-CGCCGGTGGTGCGTCCCCAGAGTAGAAACTTCG |
| 5'-5 (33mer) (SEQ ID NO: 7)<br>5'-CCTCAACGCGCCGGTGGTGCGTCCCCAGAGTAG |
| 3'-1 (33mer) (SEQ ID NO: 8)<br>5'-CCC GTC TTC CTC CTC CTA TAC TTG CAG CAA TAC |
| 3'-2 (33mer) (SEQ ID NO: 9)<br>5'-CT CCC GTC TTC CTC CTC CTA TAC TTG CAG CAA T |
| 3'-3 (33mer) (SEQ ID NO: 10)<br>5'-C GTC TTC CTC CTC CTA TAC TTG CAG CAA TACAG |
| 3'-4 (33mer) (SEQ ID NO: 11)<br>5'-CCT CCT ATA CTT GCA GCA ATA CAG CCG CCA CGC |
| 3'-5 (33mer) (SEQ ID NO: 12)<br>5'-ATC ATG CTG GCG CCC GCG TCC GCA TAC GAC TTG |

The region amplified by the primers can comprise nucleotides listed in SEQ ID NO:1, as well as subregions and partial nucleotide sequences of SEQ ID NO:1. In some embodiments the region amplified by the primers includes nucleotides 86 through 394 of SEQ ID NO:1. In some embodiments the region amplified by the primers includes of 94 through 327 of SEQ ID NO:1. In some embodiments the region amplified by the primers includes of 96 through 325 of SEQ ID NO:1. In some embodiments the region amplified by the primers includes of 108 through 323 of SEQ ID NO:1. In some embodiments the region amplified by the primers includes of 110 through 314 of SEQ ID NO:1. In one preferred embodiment, the region amplified by the primers includes nucleotides 86 through 325 of SEQ ID NO:1. In another preferred embodiment, the region amplified by the primers includes nucleotides 108 through 325 of SEQ ID NO:1.

In some embodiments one 5' and one 3' of the above primers is employed in the amplification reaction mixture. In some embodiments the upstream 5' primer is selected from the group consisting of 5'-1 (SEQ ID NO:3), 5'-2 (SEQ ID NO:4), 5'-3 (SEQ ID NO:5), 5'-4 (SEQ ID NO:6) and 5'-5 (SEQ ID NO:7). In some embodiments the downstream 3' primer is selected from the group consisting of 3'-1 (SEQ ID NO:8), 3'-2 (SEQ ID NO:9), 3'-3 (SEQ ID NO:10), 3'-4 (SEQ ID NO:11) and 3'-5 (SEQ ID NO:12). In one preferred embodiment, the 5'-1 (SEQ ID NO:3) and 3'-1 (SEQ ID NO: 8) primers are used for the amplification reaction. In another preferred embodiment, the 5'-5 (SEQ ID NO:7) and 3'-1 (SEQ ID NO:8) primer are used for the amplification reaction.

III. Amplification

Any method for polynucleotide amplification that is well known to one skilled in the art can be employed by the methods of the present invention. The amplifying step can comprise an isothermal or non-isothermal reaction such as for example but not limited to polymerase chain reaction (PCR), Scorpion™ primers, molecular beacons, SimpleProbes™, HyBeacons™, cycling probe technology, Invader Assay, self-sustained sequence replication, nucleic acid sequence-based amplification, ramification amplifying method, hybridization signal amplification method, rolling circle amplification, multiple displacement amplification, thermophilic strand displacement amplification, transcription-mediated amplification, ligase chain reaction, signal mediated amplification of RNA, split promoter amplification, Q-Beta replicase, isothermal chain reaction, one cut event amplification, loop-mediated isothermal amplification, molecular inversion probes, ampliprobe, headloop DNA amplification, and ligation activated transcription. (See, e.g., Maniatis, et al., Molecular Cloning: A Laboratory Manual, Cold Spring Harbor Lab, New York, 1982; and Innis, et al. Editor, PCR Protocols: A Guide to Methods and Applications, California, 1990; and Ausubel, et al. Editor, *Current Protocols in Molecular Biology*, USA, 1984-2008; all of which are incorporated herein by reference in their entirety.) The following examples of amplification are intended to exemplary and non-limiting.

One method for amplification can include standard polymerase chain reaction (PCR). "Polymerase chain reaction" or "PCR" means a reaction for the in vitro amplification of specific target nucleic acid sequence and is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. The reaction is cycled through different temperatures optimized for each step in a thermal cycler instrument. Particular temperatures, durations at each step, and rates of change between steps depend on many factors well known to those of ordinary skill in the art. (See, e.g., McPherson et al, editors, PCR: *A Practical Approach and PCR*2: *A Practical Approach* (IRL Press, Oxford, 1991 and 1995).

The term "PCR" further encompasses derivative forms of the reaction, including but not limited to, RT-PCR, real-time PCR, nested PCR, quantitative PCR, multiplexed PCR, and the like. "Reverse transcription PCR" or "RT-PCR" indicates a PCR that is preceded by a reverse transcription reaction that converts a target RNA to a complementary single stranded DNA, which is then amplified (see, e.g., Tecott et al, U.S. Pat. No. 5,168,038, incorporated herein by reference in its entirety). "Real-time PCR" means a PCR for which the amount of reaction product, i.e. the amplicon or amplification product, is monitored as the reaction proceeds. There are many forms of real-time PCR that differ mainly in the detection chemistries used for monitoring the reaction product (see, e.g., Gelfand et al., U.S. Pat. No. 5,210,015 (TAQ- MAN™); Wittwer et al., U.S. Pat. Nos. 6,174,670 and 6,569, 627; Tyagi et al, U.S. Pat. No. 5,925,517; Mackay et al., Nucleic Acids Research, 30: 1292-1305 (2002); all of which are incorporated herein by reference in their entirety). “Nested PCR” means a two-stage PCR wherein the amplicon of a first PCR becomes the sample for a second PCR using a new set of primers, at least one of which binds to an interior location of the first amplicon. “Multiplexed PCR” means a PCR wherein multiple target sequences (or a single target sequence and one or more reference sequences) are simultaneously carried out in the same reaction mixture (see, e.g., Bernard et al., *Anal. Biochem.,* 273: 221-228 (1999)). (See, e.g., Ausubel, et al. Editor, *Current Protocols in Molecular Biology*, USA, 1984-2008.)

Another method for amplification can include Ligase Chain Reaction. “Ligase Chain Reaction” or “LCR” refers to a method of amplification wherein two partial probes are ligated to the target nucleic acid sequence to form a new template that can then be amplified. The LCR reaction requires both DNA polymerase and DNA ligase. LCR can provide specificity for detection of single nucleotide changes. (See, e.g., Wiedmann, et al., *PCR Methods and Applications* 3(4):S51-64 (1994).)

Another method for detection can include Rolling Circle Amplification. “Rolling Circle Amplification” or “RCA” refers to an isothermal method of amplification that employs a circle of DNA, a short DNA primer (complementary to a portion of the circle) and an enzyme catalyst that converts dNTPs into a single-stranded concatameric DNA molecule that is composed of thousands of tandemly repeated copies of the circle. (See, e.g., Nallur, et al., *Nucelic Acids Res.,* 20(23): e118 (2001); Lizardi, et al., *Nature Genetics,* 19:225-232 (1998).)

Another method for amplification can include Recombinase Polymerase Amplification (Recombinase PCR Amplification, RPA), which is an isothermal amplification method. Recombinase PCR Amplification refers to a method developed by Piepenburg, Armes and colleagues (Piepenburg, et al., *PLOS Biology,* 4(7):1115-1121 (2006)), incorporated herein by reference in its entirety. RPA is a form of isothermal amplification where a recombinase-primer complex is employed to facilitate strand separation and primer binding. The recombinase-primer complexes scan double-stranded DNA and facilitate exchange at cognate sites, allowing binding of opposing oligonucleotides primers to template DNA and subsequent extension by DNA polymerase (Piepenburg, et al., *PLOS Biology,* 4(7):1115-1121 (2006)). Commercially available kits for RPA include the TwistAmp™ kits available from TwistDx (Cambridge, United Kingdom).

In addition to Recombinase Polymerase Amplification, additional isothermal amplification methods are well know in the art (Moore, Nature 435:235-238 (2005)). In Zhang et al. of (U.S. Pat. No. 7,538,202, incorporated herein by reference in its entirety) discloses methods for enzyme-free isothermal amplification.

Another isothermal amplification method employs a single-stranded “C-probe” that contains 3' and 5' sequences complementary to the target, wherein when the C-probe hybridizes with the target both ends of the probe bind close together to form a circle. This method is termed ramification amplification method, and is described in detail in Zhang et al., *Molecular Diagnosis,* 6(2):141-150 (2001), incorporated herein by reference in its entirety.

Another isothermal amplification method, termed helicase-dependent amplification (HAD) employs helicase activity to facilitate DNA unwinding and allow for amplification to occur. The method use a DNA helicase to generate single stranded templates for primer hybridization and subsequent primer extension by a DNA polymerase. (See, Vincent, et al., *EMBO Reports,* 5(8):795-800 (2004).) A kit for helicase-dependent amplification (HDA) is available from BioHelix as IsoAmpII Universal tHDA (Beverly, Mass.).

The amplifying step can be conducted on a solid support, such as a multiwell plate, array, column, bead, glass slide, polymeric membrane, glass microfiber, plastic tubes, cellulose, and carbon nanostructures or any other solid supports well known to one of skill in the art. The amplification step can further comprise an in situ hybridization step or steps.

IV. Detection

Protocols for many standard detection methods can be found for example in Maniatis, et al., Molecular Cloning: A Laboratory Manual (Cold Spring Harbor Lab, New York, 1982) and Innis, et al. Editor, PCR Protocols: A Guide to Methods and Applications, California, 1990; and Ausubel, et al. Editor, Current Protocols in Molecular Biology, USA, 1984-2008. Any well known methods of detection can be employed with the methods of the present invention.

In some embodiments, the detection step can comprise gel electrophoresis, fluorescence resonant energy transfer (FRET), or hybridization to a labeled probe, such as a probe labeled with biotin, a fluorescent moiety, an antigen, a molecular weight tag, radioactive label, or other detectable modification. In some embodiments, the detection step can comprise the incorporation of a label (such as but not limited to fluorescent or radioactive labels) during an extension reaction. The detection step can further comprise measuring fluorescence, mass, charge, and/or chemiluminescence. Any methods well known to one of skill in the art for detection of amplification products can be employed with the methods of the present invention.

a. Gel Electrophoresis

In some embodiments, amplification products can be detected by gel electrophoresis methods. The two standard types of gel electrophoresis for nucleic acid detection are polyacrylamide and agarose gel electrophoresis. (See, e.g., Maniatis, et al., Molecular Cloning: A Laboratory Manual, Cold Spring Harbor Lab, New York, 1982; and Innis, et al., PCR Protocols: A guide to Methods and Applications, California, 1990.) In some embodiments, gel electrophoresis methods can be combined with intercalators, radioactive labels, fluorescent labels and the like to facilitate detection. These methods are well known to those of skill in the art and can be employed with the methods of the present invention.

b. DNA Binding Reagents

Three general classes of fluorophores are commonly used for nucleic acid detection: intercalating dyes, minor groove binding fluorophores and other specialized stains such as for example cyanine dyes. In some embodiments, intercalating agents can be used for detection of the amplification products of the invention. Intercalating agents include but are not limited to SYBR green, SYBR gold, ethidium bromide and DRAQ5. Any intercalating agents capable of being detected and well known to one of skill in the art can be used in the methods of the present invention. In some embodiments, fluorophores that bind to the minor groove of the nucleic acid can be used for detection of the amplification products of the invention. Such fluorophores include but are not limited to Hoechst dye and SYTO17. In some embodiments, cyanine dyes can be used for detection of the amplification products of the invention. Cyanine dyes include for example but are not limited to PicoGreen, OliGreen and Ribogreen. (See, e.g., Ausubel, et al. Editor, Current Protocols in Molecular Biology, USA, 1984-2008.)

c. Real-Time Amplification

In some embodiments real-time detection of the amplification products can be performed. Real-time detection in the context of amplification indicates an amplification reaction for which the amount of reaction product, i.e. the amplicon or amplification product, is monitored simultaneously with the reaction progression. Amplification products are monitored and quantitated as the amplification products are generated in the reaction mixture. Examples of real-time detection includes RT-PCR (real-time polymerase chain reaction) and real-time quantitative PCR). (See, e.g., VanGuilder, et al., *BioTechniques,* 44:619-626 (2008); Bustin, et al., *J. Molecular Endocrinology,* 2000.)

d. TaqMan

In some embodiments, TaqMan PCR probes can be the basis for detection of the amplification products of the present invention. TaqMan probes were developed by Applied Biosystems for use with real-time PCR reactions and are commercially available from Applied Biosystems. TaqMan probes comprise an oligonucleotide sequence containing a fluorophore covalently attached to the 5'-end of the oligonucleotide probe and a quencher at the 3'-end. Several different fluorophores (including. 6-carboxyfluorescein (FAM) or tetrachlorofluorescein (TET) and quenchers (e.g., tetramethylrhodamine (TAMRA) or dihydrocyclopyrroloindole tripeptide minor groove binder (MGB)) are available for inclusion in TaqMan probes. The quencher molecule quenches the fluorescence emitted by the fluorophore when excited by an appropriate light source via FRET (Fluorescence Resonance Energy Transfer). Upon extension of the TaqMan probes by Taq polymerase, the 5' to 3' exonuclease activity of the polymerase degrades the which induces release of the fluorophore and breaks the close proximity to the quencher, thus relieving the quenching effect and allowing fluorescence of the fluorophore. Hence, fluorescence detected in the real-time PCR thermal cycler is directly proportional to the fluorophore released and the amount of DNA template present in the PCR. (See, e.g., Holland, et al., *PNAS* 88:7276-7280 (1991).)

e. Fluorescent Probes

In addition to the TaqMan fluorescent probes, other fluorescent probes can be used for detection of the amplification products of the present invention. In some embodiments, fluorescent probes can be used for detection of the amplification products. In some embodiments, fluorescence probes can be hybridized to amplification products. Fluorophores that can be used for fluorescent probes include but are not limited to DAPI (4',6-dismidino-2-phylindole; FITC (fluorescein isothiocyanate), Dil (1,1'-dihexyl-3,3,3',3'-tetramethlindocarbocyanine perchlorate), BODIPY FL and CY3, as well as any others commonly known to one of skill in the art. (See, e.g., Ausubel, et al. Editor, Current Protocols in Molecular Biology, USA, 1984-2008.)

f. Recombinase PCR Amplification (TwistDx Detection)

In some embodiments, detection can be performed using recombinase amplification methods. An example of recombinase amplification includes Recombinase PCR Amplification which refers to a method developed by Piepenburg, Armes and colleagues (Piepenburg, et al., *PLOS Biology,* 4(7):1115-1121 (2006)), incorporated herein by reference in its entirety. RPA is a form of isothermal amplification where a recombinase-primer complex is employed to facilitate strand separation and primer binding. The recombinase-primer complexes scan double-stranded DNA and facilitate exchange at cognate sites, allowing binding of opposing oligonucleotides primers to template DNA and subsequent extension by DNA polymerase (Piepenburg, et al., *PLOS Biology,* 4(7):1115-1121 (2006)). Commercially available kits for RPA include the TwistAmp™ kits available from TwistDx (Cambridge, United Kingdom).

In some embodiments the probe is labeled with a fluorophore and a quencher. In some embodiments the probe is prepared to be non-extendable by a 3'-modification group. Modification groups can include C3-spacers, a phosphate, a biotin-TEG group, an amine, or any other group well know in the art to suitable for blocking replication.

V. Kits

The methods of the present invention further provide for kits for detecting *P. ramorum* in a plant sample, said kit comprising:

an upstream and downstream amplification primer for amplifying a region of the *P. ramorum* genome within the indole-3-glycerol-phosphate synthase N-5'-phosphoribosyl anthranilate isomerase (trp1) gene and non-specific amplification reagents for amplifying the trp1 gene.

In some embodiments, the kit contains an upstream primer selected from the group consisting of 5'-1 (SEQ ID NO:3), 5'-2 (SEQ ID NO:4), 5'-3 (SEQ ID NO:5), 5'-4 (SEQ ID NO:6) and 5'-5 (SEQ ID NO:7), and a downstream primer selected from the group consisting of 3'-1 (SEQ ID NO:8), 3'-2 (SEQ ID NO:9), 3'-3 (SEQ ID NO:10), 3'-4 (SEQ ID NO:11) and 3'-5 (SEQ ID NO:12).

In some embodiments, the kit contains an upstream primer selected from the group consisting of 5'-1 (SEQ ID NO:3) and 5'-5 (SEQ ID NO:7), and a downstream primer selected from the group consisting of 3'-1 (SEQ ID NO: 8).

In some embodiments, the kit further comprises a nucleic acid probe that hybridizes to the amplified region of the trp1 gene. In some embodiments, the kit further comprises a nucleic acid probe that hybridizes to the amplified region of the trp1 gene and binds to nucleotides 163 to 213 of SEQ ID NO:1. In some embodiments, the kit further comprises a nucleic acid probe that comprises SEQ ID NO:2 or a probe substantially identical to SEQ ID NO:2. In some embodiments, the kit further comprises a nucleic acid probe that is fluorescently labeled. In some embodiments, the kit further comprises a nucleic acid probe that is capable of being labeled by any means well known to one of skill in the art.

In some embodiments, the kit further comprises non-specific amplification reagents. In some embodiments, the kit further comprises bacterial recombinase. In some embodiments, the kit further comprises a DNA intercalating agent for detection of the amplified DNA.

EXAMPLES

The following examples are offered to illustrate, but not to limit the claimed invention.

Example 1

Sample DNA Preparation.

DNA samples were prepared using DNA isolation kit (Product #26200) obtained from Norgen Bioteck Corporation (Ontario, Canada). The sample isolates were obtained from both Europe and the United States. The kit provides for preparation of DNA from plant and filamentous fungi species. The kit further provides for detection of pathogens which may be infecting a plant, as it allows for the purification of any pathogen DNA along with the purification of the total DNA.

Lysate Preparation.

All centrifugation spins are carried out in a benchtop microcentrifuge at 14,000×g (~14,000 RPM) except where otherwise noted. Approximately, $5\times10^6$ 50 mg of plant tissue (less than or equal to 50 mg) is transferred into a mortar that contains 500 µL of Lysis Solution (with RNAase added). The samples are then ground until the tissue is completely macerated. Alternatively, other homogenization methods can be used with this procedure, including grinding with liquid nitrogen or a bead system. If an alternative method is used, add 500 µL of Lysis Solution to the sample immediately after homogenization and vortex for 20 seconds to mix. Next, add 100 µL of Lysis Additive and vortex briefly. Incubate mixture at 65° C. for 10 minutes. Occasionally mix the lysate 2 or 3 times during the incubation period by inverting the tube. Add 100 µL of Binding Solution, mix and incubate the mixture for 10 minutes on ice. The lysate is then spun for 5 minutes to pellet any cell debris. Using a pipette, the lysate is then transferred using a pipette into a DNAase-free microcentrifuge tube, ensuring that only the clear lysate underneath of the layer is transferred. Small amounts of debris will not affect the DNA isolation and quality. Repeat the last 5 minute spin and lysate transfer as necessary. Add an equal volume of 70% ethanol (provided by the user) to the lysate collected (100 µL of ethanol is added to every 100 µL of lysate), vortex to mix.

Binding to Column.

Assemble a column with one of the collection tubes provided in the Norgen Plant/Fungi Isolation kit. Apply up to 600 µL of the clarified lysate mixed with ethanol onto the column and centrifuge for 1 minute at 14,000×g (~14,000 RPM). Discard the flowthrough and reassemble the spin column with the collection tube. Ensure the entire lysate volume has passed through into the collection tube by inspecting the column. If the entire lysate volume has not passed, spin for an additional minute. Depending on your lysate volume, repeat column spin step as necessary.

Column Wash.

Apply 500 µL of Wash Solution to the column and centrifuge for 1 minute, ensuring the entire wash solution has passed through into the collection tube by inspecting the column. If the entire wash volume has not passed, spin for an additional minute. Discard the flowthrough and reassemble the spin column with its collection tube. Apply 500 µL of Wash Solution to the column and centrifuge for 1 minute. Discard the flowthrough and reassemble the spin column with its collection tube. Spin the column for 2 minutes in order to thoroughly dry the resin. Discard the collection tube.

DNA Elution.

Place the column into a fresh 1.7 mL Elution tube provided with the kit. Add 100 µL of Elution Buffer to the column. Centrifuge for 2 minutes at 200×g (~2,000 RPM), followed by a 1 minute spin at 14,000×g (~14,000 RPM). Note the volume eluted from the column. If the entire volume has not been eluted, spin the column at 14,000×g (~14,000 RPM) for 1 additional minute. An additional elution may be performed if desired by repeating the wash and centrifuge steps using 50 µL of Elution Buffer. The total yield can be improved by an additional 20-30% when this second elution is performed.

Example 2

Recombinase PCR Amplification (RPA) Detection of *Phytophthora ramorum*.

Specific identification of *Phytophthora ramorum* was performed using the TwistDx TwistAmp™ EXO Kit.

Primers and Probe.

Primers (five 5' and five 3') were designed for amplification of the region of interest. These primers are designated 5'-1 through 5'-5 (upstream, forward primers; SEQ ID NOS:3-7) and 3'-1 through 3'-5 (downstream reverse primers; SEQ ID NOS:8-12). One detection probe was designed and prepared based on the manufacturer's suggestions. The detection probe, Probe-r (SEQ ID NO:2), contains an abasic nucleotide analogue, a tetrahydrofuran residue, THF, also called dSpacer), flanked by a dT-TAMRA (fluorophore) and a dT-BHQ2 (quencher). In addition the probe was prepared to be non-extendable by the addition of $C_3$-spacer 3'-modification group.

Initial Testing.

The initial testing of the TwistDx™ TwistAmp EXO Kit (Product Code: TW101; TwistDx Ltd., Cambridge, United Kingdom), primers, and probe utilized the 5'-1 (SEQ ID NO:3)/3'-1 (SEQ ID NO:8) primer pairing and conditions suggested by the manufacturer. To the template sample DNA prepared in Example 1, suspended in elution buffer, rehydration solution was added. The rehydration solution includes: the TwistAmp™ Exo rehydration buffer (29.5 µL), the amplification primers (2.1 µL of each primer to a final concentration of 10 µM for each primer), the detection probe Probe-r (0.6 µL to a final concentration of 10 µM; SEQ ID NO:2) and sample DNA dissolved in $dH_2O$ (13.2 µL) for a total volume of 47.5 µL. The reaction was then initiated by addition of 2.5 µL of 280 mM magnesium-acetate solution provided by the kit, to bring the total reaction volume to 50 µL. The total reaction was then mixed thoroughly. Once mixed, the reaction is placed directly into the Twista™ tube scanner for real-time fluorescence monitoring. Tubes were maintained at 39° C. during the scanning period. After the initial 4 minutes of the Twista™ scanning period, samples were removed, vortexed, briefly centrifuged and then returned to the sample reader in their original positions and scanned for a total incubation and detection period of 20 minutes.

Samples used for the recombinant PCR amplification (RPA) reactions were obtained from a cultured mycelium of a group of twelve *Phytophthora* and *Pythium* species, from which DNA was purified as described in Example 1 above.

The first test samples were comprised of one each of *P. ramorum*, *P. lateralis*, and *P. helicoides* at two different concentrations of DNA. As shown in FIG. 1, the RPA test demonstrated specificity for the *P. ramorum* strain.

Figure 2:
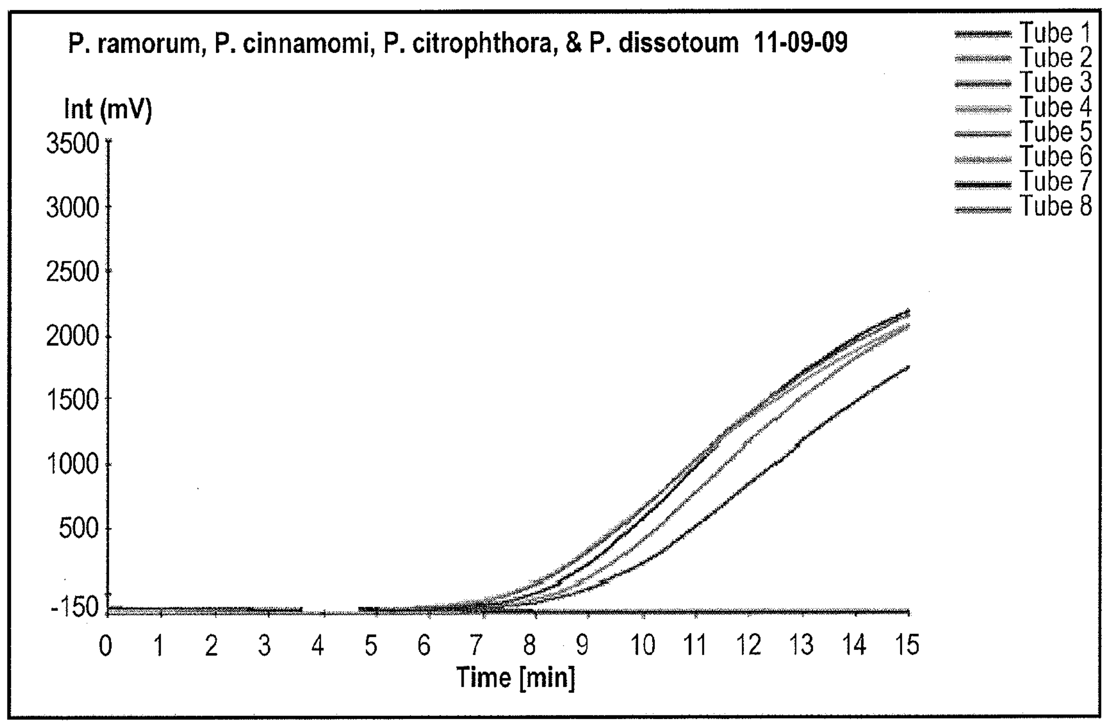
FIG. 2: Specific Detection of *P. ramorum* using TwistAmp™.
Figure 3:
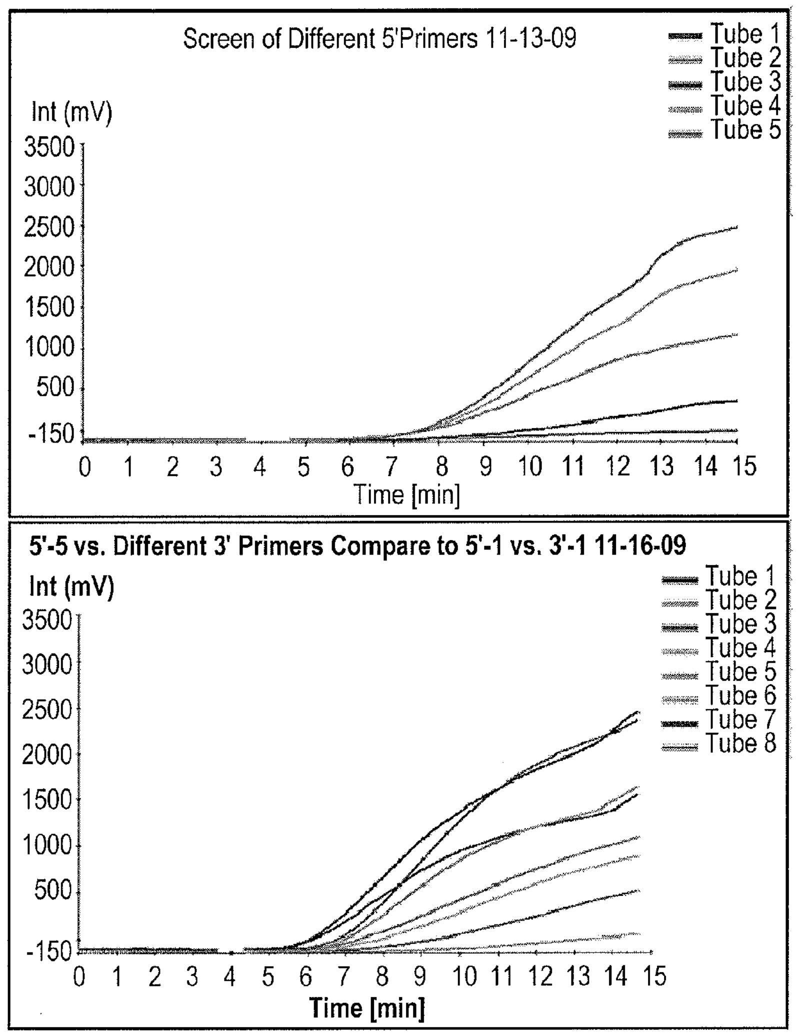
FIG. 3: Primer Optimization for Detection of *P. ramorum* using TwistAmp™.

In order to confirm the specificity of the test additional *P. ramorum*, non-*ramorum Phytophthora* species and *Pythium* species were also tested using the Recombinase PCR amplification assay to determine whether there was non-specific detection of these non-*P. ramorum* organisms. The assay continued to demonstrate specificity for *P. ramorum*, as seen in FIG. 2.

Primer Screening.

Figure 4A:
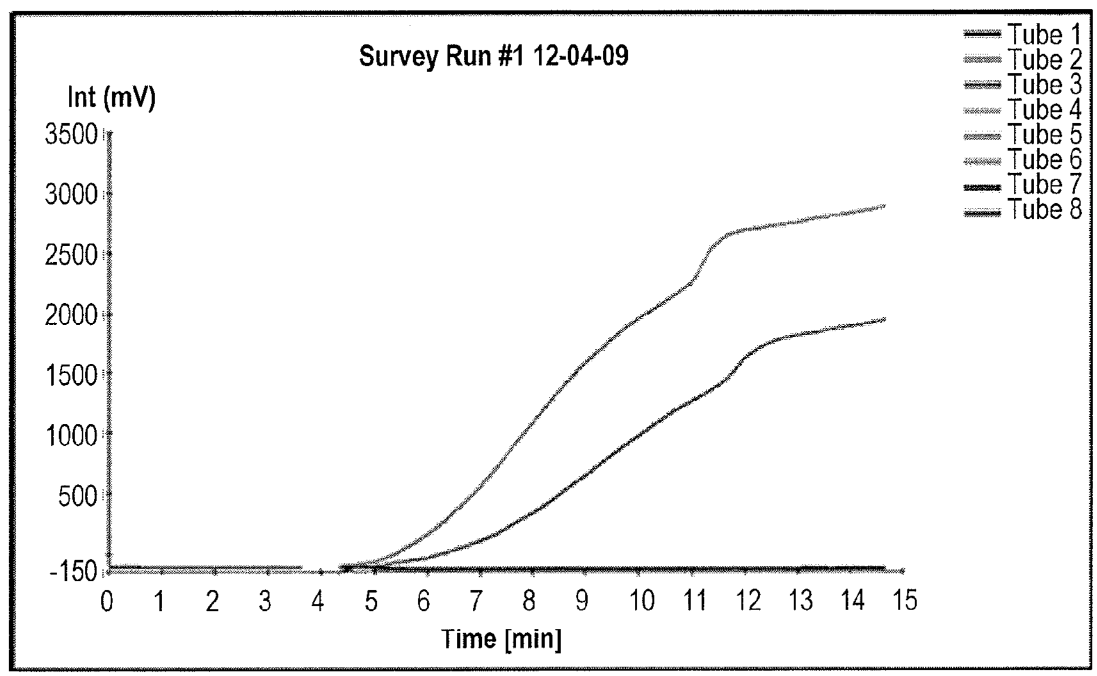
FIG. 4: Large Scale Survey of TwistAmp™ Specific Detection of *P. ramorum*.
(FIG. 4F). The oligonucleotide set consisting of primers 5'-1 (SEQ ID NO:3) and 3'-1 (SEQ ID NO:8) and the TAMRA labeled Probe-r (SEQ ID NO:2) is capable of specific identification of trp1 from *P. ramorum* in the presence of the closely related *P. cryptogea, P. palmivora, P. megasperma, P. hungarica, P. tropicalis*, as well as in the presence of *Pythium* species (FIG. 4G). The oligonucleotide set consisting of primers 5'-1 (SEQ ID NO:3) and 3'-1 (SEQ ID NO:8) and the TAMRA labeled Probe-r (SEQ ID NO:2) is capable of specific identification of trp1 from *P. ramorum* in the presence of the closely related *P. richardiae, P. cactorum, P. citricola, Phytophthora* species ID P8219, *Phytophthora* species sinensis-type and *P. megasperma* (FIG. 4H). The oligonucleotide set consisting of primers 5'-1 (SEQ ID NO:3) and 3'-1 (SEQ ID NO:8) and the TAMRA labeled Probe-r (SEQ ID NO:2) is capable of specific identification of trp1 from *P. ramorum* in the presence of the closely related *Phytophthora* species ID P8219, *P. sojae, Phytophthora* species sinensis-type, *P. palmivora, P. cryptogea, Phytophthora* species ID P10665, and *Phytophthora* species citricola-type (FIG. 4I). The oligonucleotide set consisting of primers 5'-1 (SEQ ID NO:3) and 3'-1 (SEQ ID NO:8) and the TAMRA labeled Probe-r (SEQ ID NO:2) is capable of specific identification of trp1 from *P. ramorum* in the presence of two closely related *P. cactorum* species, two closely related *P. megasperma* species, as well as *P. gonapodyides, P. sojae* and *P. heveae* (FIG. 4J).
Figure 4E:
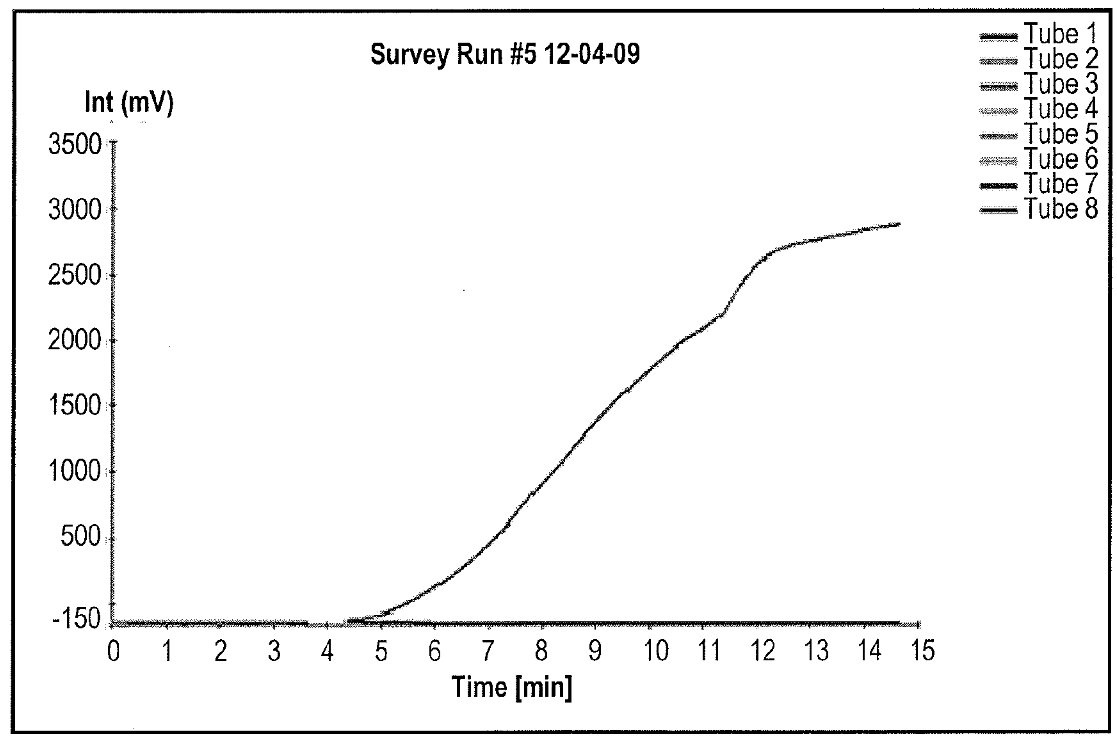
Figure 4I:
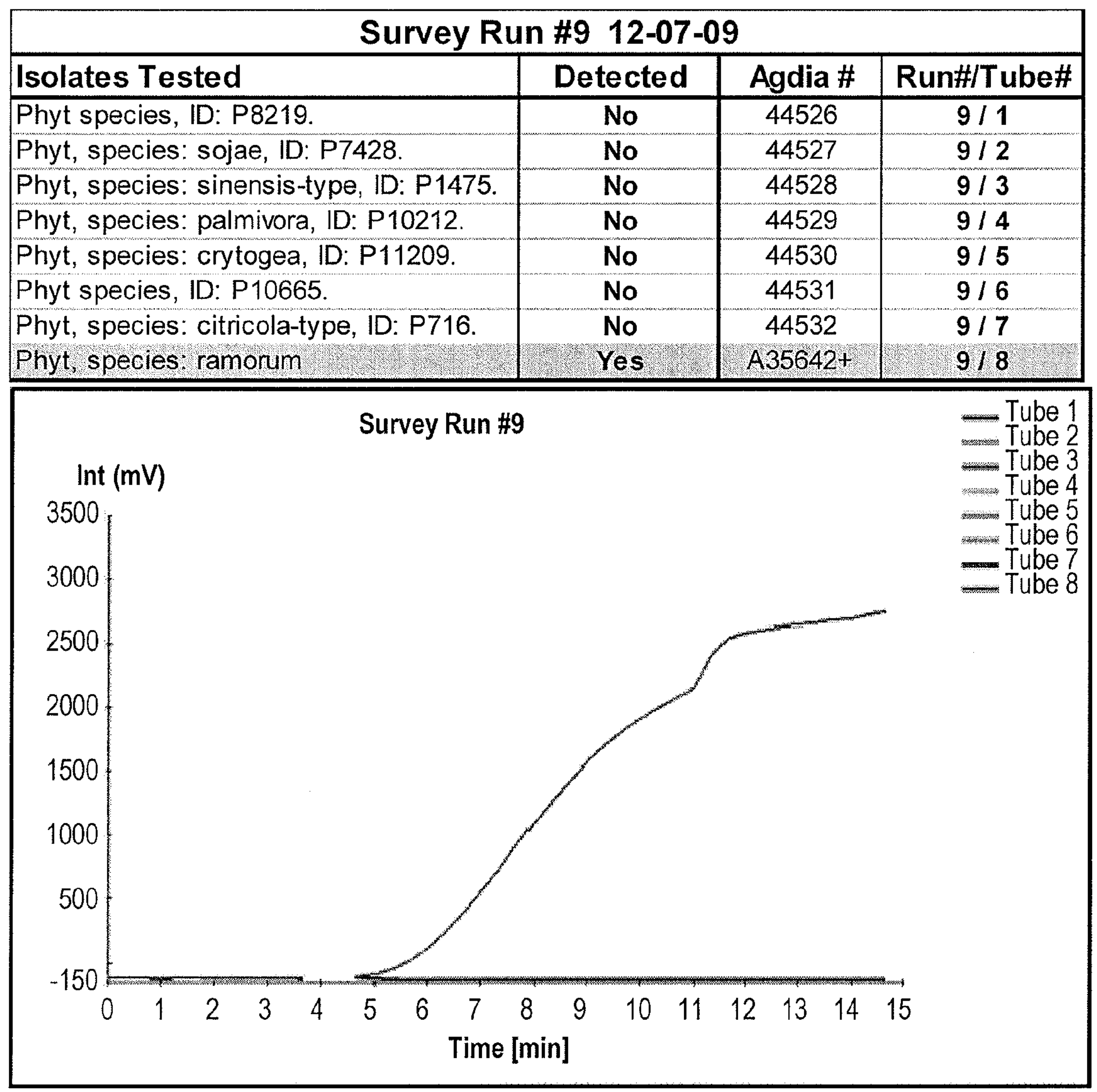

Different combinations of primers were screened in the RPA assay to determine if one pairing was optimal with respect to other pairings. First, all 5' primers (SEQ ID NOS: 3-7) were paired with primer 3'-1 (SEQ ID NO:8). The optimal 5' primer was the selected as 5'-1 (SEQ ID NO:3) and paired with all 3' primers (SEQ ID NOS:8-12). All combinations were tested in the RPA assay against *P. ramorum* strain A35642 and were compared to the original primer pair 5'-1 (SEQ ID NO:3)/3'-1 (SEQ ID NO:8). Primer 5'-5 (SEQ ID NO:7) worked well with 3'-1 (SEQ ID NO:8), giving final readings similar to 5'-1 (SEQ ID NO:3)/3'-1 (SEQ ID NO:8). No primer from the 3' region performed as well as 3'-1 (SEQ ID NO:8). Final analysis of reactivity showed the original pair, 5'-1 (SEQ ID NO:3)/3'-1 (SEQ ID NO:8), produced faster amplification, potentially translating to a more rapid and sensitive test. The data showing the primer combination is included in FIG. 4.

Large Scale Survey.

Final examination and evidence of assay specificity was demonstrated by surveying additional *Phytophthora* and *Pythium* isolates of known identity using the primer pair 5'-1

(SEQ ID NO:3)/3'-1 (SEQ ID NO:8) for detection of *P. ramorum*. Using the methods of the TwistDx™ TwistAmp EXO assay, no detection of any isolate not known to be *P. ramorum* occurred. The results of this survey, combined with previous results, is included in FIG. 5.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of specifically detecting the presence of *Phytophthora ramorum* in a biological sample, the method comprising:

(i) amplifying a region of the *P. ramorum* genome within the indole-3-glycerol-phosphate synthase N-5'-phosphoribosyl anthranilate isomerase (trp1) gene using an isothermal amplification system and a primer pair where the primer pair is 5'-1 (SEQ ID NO:3) and 3'-1 (SEQ ID NO:8), or 5'-5 (SEQ ID NO:7) and 3'-1 (SEQ ID NO:8); and, (ii) detecting the amplification product.

2. A method of claim 1 wherein the amplifying is by recombinase PCR.

3. A method of claim 1 wherein the primers are: 5'-1 (SEQ ID NO:3) and 3'-1 (SEQ ID NO:8).

4. A method of claim 1 wherein the primers are: 5'-5 (SEQ ID NO:7) and 3'-1 (SEQ ID NO:8).

5. A method of claim 1 wherein the detecting uses a fluorescent probe.

6. A method of claim 5 wherein the fluorescent probe binds to nucleotides 163 to 213 of SEQ ID NO:1.

7. A method of claim 5 wherein the fluorescent probe comprises SEQ ID NO:2.

8. A method of claim 1 wherein the detection is in real time.

9. A method of claim 1 wherein the sample is from the genus *Quercus*.

10. A method of claim 1 further comprising a DNA intercalating agent to detect amplified DNA.

* * * * *

SEQUENCE LISTING

```
<160> NUMBER OF SEQ ID NOS: 12

<210> SEQ ID NO 1
<211> LENGTH: 807
<212> TYPE: DNA
<213> ORGANISM: Phytophthora ramorum
<220> FEATURE:
<223> OTHER INFORMATION: Phytophthora ramorum isolate PR-05-012
      haplotype EU1-B indole-3-glycerol-phosphate synthase
      N-5'-phosphoribosyl anthranilate isomerase (trp1,
      TRP1, IGPS-PRAI), partial sequence

<400> SEQUENCE: 1

agcaggtcgt gacgcccgag cagctggtga agaagatcga gagcaccgag agtgtctacg     60

gctcggccct gcgcgtgctc gaccgcctca acgcgccggt ggtgcgtccc cagagtagaa    120

acttcgggaa tggacgaggc tgacggctgt cgttgcattg ttcctattgt tgtattgcaa    180

tatcacagaa ggaaggctgg tcggacgtgg cgctggcagc cgagttcaag cgcgccagcc    240

ccagcaaggg agatatcgcc acgggactca acctgcgcgg tgcgtggcgg ctgtattgct    300

gcaagtatag gaggaggaag acgggagcta atgtgatttt tgcaatggga gcagagcaag    360

tcaagtcgta tgcggacgcg ggcgccagca tgatctccgt gctgacggag cccaagtggt    420

tcaagggctc attggaggac atgatggcgg ccagagacgt ggtggagagc atgagcgctc    480

gccccgccat cctccgcaag gacttcatta tcgacgtgta ccagctgctg gaggctcgcg    540

cctacggagc cgactgtgtg ctgctcattg tggcgctgct gtcccaggag cagctcgttg    600

agctcattga tgcaagtagc tgcgttaatg agccgaactt tctgacgaga ggatgaatgt    660

tgacgttgag tttgtgtctg ctttgcattg tgcaggcaac tcacaacctc ggcatgtgcg    720

ccttagtgga ggtgaacagc gttgaggagc tggacatcgc gctggctgcc aggtcgcgcc    780

tgattggcgt caataaccga gacctcc                                        807


<210> SEQ ID NO 2
<211> LENGTH: 51
<212> TYPE: DNA
<213> ORGANISM: Artificial Sequence
<220> FEATURE:
<223> OTHER INFORMATION: synthetic TAMRA labeled fluorescent detection
      probe (reverse strand), Probe-r
<220> FEATURE:
<221> NAME/KEY: modified_base
<222> LOCATION: (32)...(32)
<223> OTHER INFORMATION: n = t modified by tetramethylrhodamine (TAMRA)
<220> FEATURE:
<221> NAME/KEY: modified_base
<222> LOCATION: (33)...(33)
<223> OTHER INFORMATION: n = abasic nucleotide analogue,
      tetrahydrofuran (THF) derivative, dSpacer
<220> FEATURE:
<221> NAME/KEY: modified_base
<222> LOCATION: (35)...(35)
<223> OTHER INFORMATION: n = t modified by Black Hole Quencher 2 (BHQ2)
<220> FEATURE:
<221> NAME/KEY: modified_base
<222> LOCATION: (51)...(51)
<223> OTHER INFORMATION: g modified by 3' C-3-spacer, 1,3-propanediol
```

```
<400> SEQUENCE: 2

gcgccacgtc cgaccagcct tccttctgtg anntngcaat acaacaatag g              51


<210> SEQ ID NO 3
<211> LENGTH: 33
<212> TYPE: DNA
<213> ORGANISM: Artificial Sequence
<220> FEATURE:
<223> OTHER INFORMATION: synthetic upstream, forward oligonucleotide
      amplification 5' twisted primer 5'-1

<400> SEQUENCE: 3

ccccagagta gaaacttcgg gaatggacga ggc                                  33


<210> SEQ ID NO 4
<211> LENGTH: 33
<212> TYPE: DNA
<213> ORGANISM: Artificial Sequence
<220> FEATURE:
<223> OTHER INFORMATION: synthetic upstream, forward oligonucleotide
      amplification 5' twisted primer 5'-2

<400> SEQUENCE: 4

ccagagtaga aacttcggga atggacgagg ctg                                  33


<210> SEQ ID NO 5
<211> LENGTH: 33
<212> TYPE: DNA
<213> ORGANISM: Artificial Sequence
<220> FEATURE:
<223> OTHER INFORMATION: synthetic upstream, forward oligonucleotide
      amplification 5' twisted primer 5'-3

<400> SEQUENCE: 5

ccggtggtgc gtccccagag tagaaacttc ggg                                  33


<210> SEQ ID NO 6
<211> LENGTH: 33
<212> TYPE: DNA
<213> ORGANISM: Artificial Sequence
<220> FEATURE:
<223> OTHER INFORMATION: synthetic upstream, forward oligonucleotide
      amplification 5' twisted primer 5'-4

<400> SEQUENCE: 6

cgccggtggt gcgtccccag agtagaaact tcg                                  33


<210> SEQ ID NO 7
<211> LENGTH: 33
<212> TYPE: DNA
<213> ORGANISM: Artificial Sequence
<220> FEATURE:
<223> OTHER INFORMATION: synthetic upstream, forward oligonucleotide
      amplification 5' twisted primer 5'-5

<400> SEQUENCE: 7

cctcaacgcg ccggtggtgc gtccccagag tag                                  33


<210> SEQ ID NO 8
<211> LENGTH: 33
<212> TYPE: DNA
<213> ORGANISM: Artificial Sequence
<220> FEATURE:
<223> OTHER INFORMATION: synthetic downstream, reverse oligonucleotide
      amplification 3' twisted primer 3'-1

<400> SEQUENCE: 8
```

-continued

```
cccgtcttcc tcctcctata cttgcagcaa tac                                  33


<210> SEQ ID NO 9
<211> LENGTH: 33
<212> TYPE: DNA
<213> ORGANISM: Artificial Sequence
<220> FEATURE:
<223> OTHER INFORMATION: synthetic downstream, reverse oligonucleotide
      amplification 3' twisted primer 3'-2

<400> SEQUENCE: 9

ctcccgtctt cctcctccta tacttgcagc aat                                  33


<210> SEQ ID NO 10
<211> LENGTH: 33
<212> TYPE: DNA
<213> ORGANISM: Artificial Sequence
<220> FEATURE:
<223> OTHER INFORMATION: synthetic downstream, reverse oligonucleotide
      amplification 3' twisted primer 3'-3

<400> SEQUENCE: 10

cgtcttcctc ctcctatact tgcagcaata cag                                  33


<210> SEQ ID NO 11
<211> LENGTH: 33
<212> TYPE: DNA
<213> ORGANISM: Artificial Sequence
<220> FEATURE:
<223> OTHER INFORMATION: synthetic downstream, reverse oligonucleotide
      amplification 3' twisted primer 3'-4

<400> SEQUENCE: 11

cctcctatac ttgcagcaat acagccgcca cgc                                  33


<210> SEQ ID NO 12
<211> LENGTH: 33
<212> TYPE: DNA
<213> ORGANISM: Artificial Sequence
<220> FEATURE:
<223> OTHER INFORMATION: synthetic downstream, reverse oligonucleotide
      amplification 3' twisted primer 3'-5

<400> SEQUENCE: 12

atcatgctgg cgcccgcgtc cgcatacgac ttg                                  33
```